(12) United States Patent
Wenzel et al.

(10) Patent No.: US 8,092,386 B1
(45) Date of Patent: Jan. 10, 2012

(54) METHOD AND IMPLANTABLE SYSTEM FOR BLOOD-GLUCOSE CONCENTRATION MONITORING

(75) Inventors: Brian J. Wenzel, San Jose, CA (US); Taraneh Ghaffari Farazi, San Jose, CA (US)

(73) Assignee: Pacesetter, Inc., Sunnyvale, CA (US)

(*) Notice: Subject to any disclaimer, the term of this patent is extended or adjusted under 35 U.S.C. 154(b) by 1348 days.

(21) Appl. No.: 11/615,591

(22) Filed: Dec. 22, 2006

(51) Int. Cl.
*A61B 5/00* (2006.01)

(52) U.S. Cl. ......... 600/365; 600/316; 600/322; 600/323

(58) Field of Classification Search .................. 600/301, 600/322–341, 365, 500, 502, 504–507, 509, 600/347, 316
See application file for complete search history.

(56) References Cited

U.S. PATENT DOCUMENTS

| | | | |
|---|---|---|---|
| 4,685,463 A * | 8/1987 | Williams ...................... | 600/365 |
| 4,731,051 A | 3/1988 | Fischell | |
| 4,776,340 A * | 10/1988 | Moran et al. .................. | 600/327 |
| 4,809,697 A | 3/1989 | Causey, III et al. | |
| 4,815,469 A | 3/1989 | Cohen et al. | |
| 4,869,254 A | 9/1989 | Stone et al. | |
| 4,944,299 A | 7/1990 | Silvian | |
| 4,947,845 A | 8/1990 | Davis | |
| 5,078,136 A | 1/1992 | Stone et al. | |
| 5,497,772 A * | 3/1996 | Schulman et al. ............. | 600/347 |
| 5,615,671 A * | 4/1997 | Schoonen et al. ............. | 600/322 |
| 5,730,125 A * | 3/1998 | Prutchi et al. ................. | 600/323 |
| 5,795,305 A | 8/1998 | Cho et al. | |
| 5,919,216 A | 7/1999 | Houben et al. | |
| 5,924,996 A | 7/1999 | Cho et al. | |
| 6,122,536 A * | 9/2000 | Sun et al. ...................... | 600/341 |
| 6,169,925 B1 * | 1/2001 | Villaseca et al. .............. | 607/60 |
| 6,233,471 B1 * | 5/2001 | Berner et al. .................. | 600/345 |
| 6,275,734 B1 | 8/2001 | McClure et al. | |
| 6,409,675 B1 | 6/2002 | Turcott | |
| 6,491,639 B1 | 12/2002 | Turcott | |

(Continued)

FOREIGN PATENT DOCUMENTS

EP 1495714 1/2005

OTHER PUBLICATIONS

Cho et al., "Noninvasive Measurement of Glucose by Metabolic Heat Conformation Method," Oak Ridge Conference, Clinical Chemistry, pp. 1894-1989, (2004).

*Primary Examiner* — Patricia Mallari
(74) *Attorney, Agent, or Firm* — Steven M. Mitchell

(57) ABSTRACT

In an implantable medical device for monitoring blood-glucose concentration in the blood, metabolic oxygen consumption is derived by measuring physiological metrics related to mixed venous oxygen concentration. Blood-glucose concentration is determined using correlations of blood-glucose concentration with measures of metabolic oxygen consumption including oxymetric, temperature, and electrocardiographic data. Additional physiological sensor measurements may be used to enhance the accuracy of the analysis of blood-glucose concentration. By using a combination of oxymetric and other physiological metrics, blood-glucose concentration can be reliably calculated over a wide range. The device compares the blood-glucose concentration with upper and lower acceptable bounds and generates appropriate warning signals if the concentration falls outside the bounds. The device may also control a therapeutic device to maintain blood-glucose concentration within an acceptable range. A calibration technique determines patient-specific parameters for use in the calculation of blood-glucose concentration.

37 Claims, 8 Drawing Sheets

U.S. PATENT DOCUMENTS

| | | |
|---|---|---|
| 6,546,268 B1 * | 4/2003 | Ishikawa et al. .............. 600/345 |
| 6,572,542 B1 | 6/2003 | Houben et al. |
| 6,878,135 B1 | 4/2005 | Haller et al. |
| 6,944,448 B1 * | 9/2005 | Bobst ........................... 455/424 |
| 6,944,488 B2 * | 9/2005 | Roberts ........................ 600/339 |
| 6,954,661 B2 * | 10/2005 | Cho et al. ..................... 600/316 |
| 6,954,662 B2 | 10/2005 | Freger et al. |
| 6,970,742 B2 | 11/2005 | Mann et al. |
| 7,016,720 B2 | 3/2006 | Kroll |
| 7,029,443 B2 | 4/2006 | Kroll |
| 7,039,446 B2 | 5/2006 | Ruchti et al. |
| 2002/0120186 A1 * | 8/2002 | Keimel ......................... 600/365 |
| 2003/0125612 A1 * | 7/2003 | Fox et al. ...................... 600/347 |
| 2003/0208113 A1 * | 11/2003 | Mault et al. ................... 600/316 |
| 2004/0078065 A1 * | 4/2004 | Kroll ............................. 607/60 |
| 2004/0127777 A1 | 7/2004 | Ruchti et al. |
| 2005/0027182 A1 * | 2/2005 | Siddiqui et al. .............. 600/365 |
| 2005/0288722 A1 | 12/2005 | Eigler et al. |
| 2006/0084854 A1 | 4/2006 | Cho et al. |
| 2006/0167519 A1 | 7/2006 | Gill et al. |
| 2008/0275317 A1 * | 11/2008 | Cho et al. ..................... 600/310 |

* cited by examiner

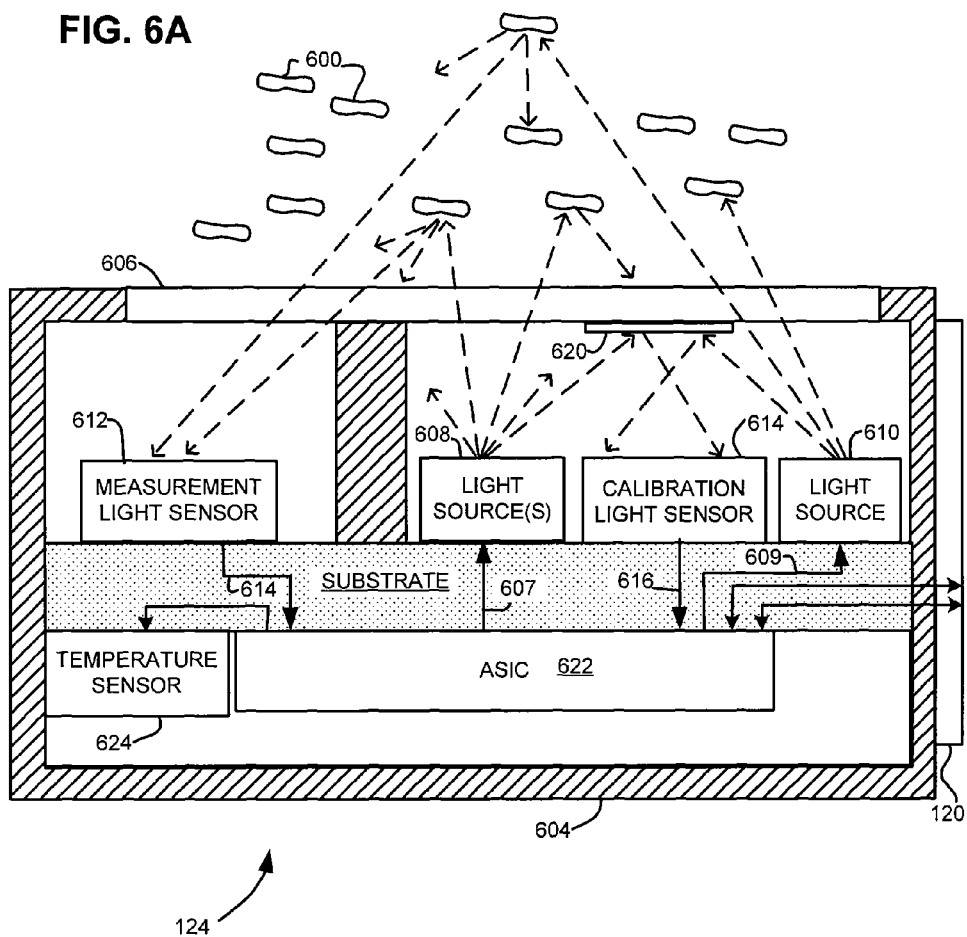

FIG. 6B
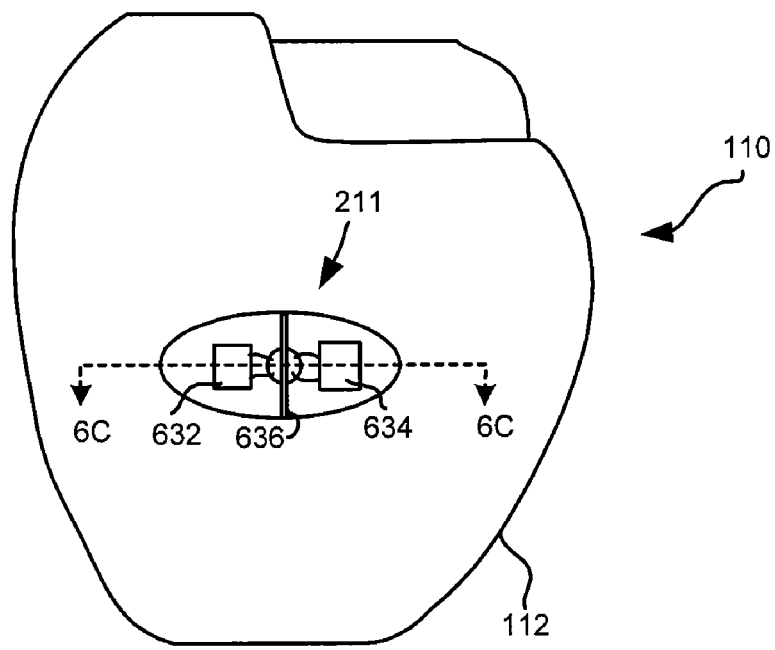
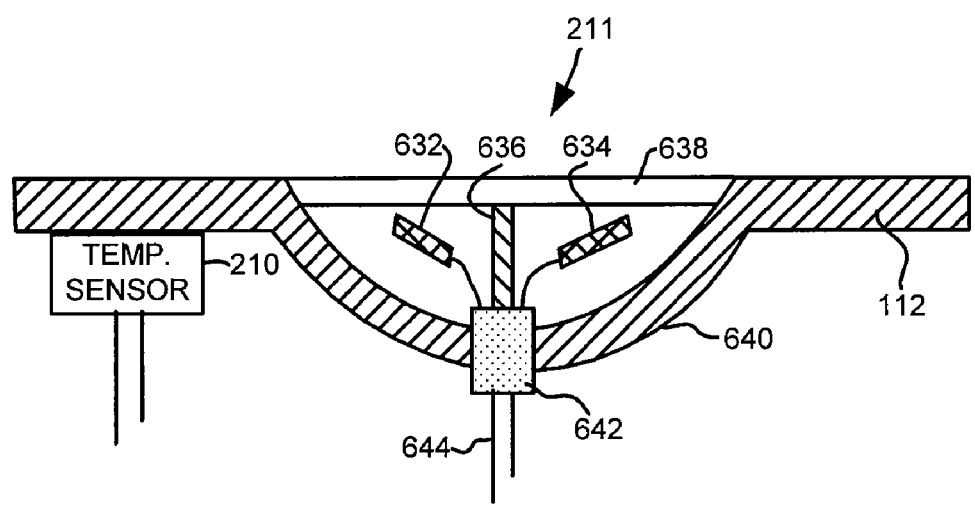
FIG. 6C

METHOD AND IMPLANTABLE SYSTEM FOR BLOOD-GLUCOSE CONCENTRATION MONITORING

FIELD OF THE INVENTION

Embodiments of the present invention relate to methods and implantable systems for obtaining measures of blood-glucose concentration utilizing the metabolic oxygen conformation method.

BACKGROUND OF INVENTION

Eighteen million Americans suffer from diabetes. Diabetes is a life-long disease marked by high concentrations of glucose in the blood. The sugar called glucose enters the bloodstream when food is digested. Glucose is a source of fuel for the body. In response to the glucose in the bloodstream, an organ called the pancreas makes the hormone insulin. The role of insulin is to move glucose from the bloodstream into muscle, fat, and liver cells, where it can be used as fuel. Individuals with diabetes either do not produce insulin (Type I diabetes) or are resistant to insulin (Type II diabetes). Consequently, the concentration of glucose in the blood in a person with diabetes may vary by a large amount dependent upon what they have eaten and the person's metabolic requirements.

There is no cure for diabetes. The goal of diabetes treatment is to stabilize the patient's blood-glucose concentration and eliminate the symptoms of high blood-glucose concentration. In order to control the patient's blood-glucose concentration, diabetics have to regularly monitor their blood-glucose concentration. If the patient's blood-glucose concentration is too high, they need an injection of insulin. If the patient's blood-glucose concentration is too low, they need to eat something with glucose in it. Blood-glucose concentration changes rapidly and the consequences of not controlling it properly can be immediate. A high concentration of glucose in the blood, termed hyperglycemia, can cause several problems including: frequent urination, excessive thirst, hunger, fatigue, weight loss, and blurry vision. A low concentration of glucose in the blood, termed hypoglycemia, can cause diabetic shock, coma and death. Poor blood-glucose concentration regulation also has long-term effects on health. Over the long-term, poor blood-glucose concentration regulation in diabetics can cause complications such as heart disease and kidney failure. Diabetes has high comorbidity with cardiac disease. Up to 45% of individuals with bradycardia or tachycardia also suffer from diabetes.

In order to reduce the risk of long-term complications from diabetes, the American Diabetes Association recommends that pre-meal blood-glucose concentrations fall in the range of 80 to 120 mg/dL and bedtime blood concentrations fall in the range of 100 to 140 mg/dL. Physicians also measure hemoglobin A1c (HbA1c) level. The HbA1c is a measure of average blood-glucose concentration during the previous two to three months. It is a useful way to monitor a patient's overall response to diabetes treatment over time. A person without diabetes has an HbA1c around 5%. People with diabetes should try to keep it below 7%. Studies have found dramatically lower rates of kidney, eye, and nervous system complications in patients with tight control of blood-glucose concentration. In addition, such control causes a significant drop in all diabetes-related deaths, including lower risks of heart attack and stroke.

Thus, it is important to keep a patient's blood-glucose concentration near normal concentrations. However, with blood-glucose kept at near normal concentrations, diabetics are at higher risk of hypoglycemia as the glucose becomes depleted over time. Blood-glucose concentration monitoring is the critical first step that allows diabetics to control their blood-glucose concentration. Typically, a sample of blood must be drawn and then the blood-glucose concentration assayed using color changing strips or an electrical device. To ensure proper dosage of insulin, individuals with diabetes use lancets to draw blood for conventional glucose measurements. A disadvantage of current blood-glucose concentration testing is that the painful process of drawing blood limits the number of times an individual is willing to take measurements. It is also a disadvantage that the process requires active user intervention.

A method for external monitoring of blood-glucose concentration without drawing blood is disclosed in a publication by Cho et al., entitled "Noninvasive Measurement of Glucose by Metabolic Heat Conformation Method," Clinical Chemistry 50:10 1894-1898 (2004), which is incorporated herein by reference. This publication utilizes a metabolic heat conformation method which depends upon measuring body surface temperature and conductive and radiative heat losses from the subject. These heat losses are tied through the circulatory system to glucose metabolism, which is the primary source of heat generation in the body. Using analysis of the surface temperature measurements and external peripheral measurements of blood flow, hematocrit and oxygen saturation, and standard blood-glucose concentration measurements, the authors developed relationships between the external measurements that predicted measured blood-glucose concentration. The MHC method utilizes precise measurements of external heat loss to estimate the rate of glucose metabolism and then correlates that to the blood-glucose concentration. However, while the method disclosed by Cho et al. has the advantage that it does not require blood to be drawn, it still requires active user intervention. See, also, U.S. Pat. No. 5,795,305 entitled "Process And Device For Non-Invasive Determination Of blood-glucose concentration In Parts Of The Human Body" to Cho et al.; and U.S. Pat. No. 5,924,996 titled "Process And Device For Detecting The Exchange Of Heat Between The Human Body And The Invented Device And Its Correlation To The blood-glucose concentration In Human Blood" to Cho et al. both of which are incorporated herein by reference. Moreover, the method disclosed by Cho, because it requires external measurements of the heat lost at the surface of the human body, cannot be utilized in an implantable device.

In view of the many disadvantages of conventional external blood-glucose concentration monitoring techniques, implantable blood-glucose concentration monitors have been developed, which include sensors for mounting directly within the blood stream. Most implantable glucose sensors are amperometric enzymatic biosensors which use immobilized glucose oxidase, an enzyme that catalyzes the oxidation of glucose to gluconic acid with the production of hydrogen peroxide. However, such amperometric enzymatic biosensors tend to clog very quickly. Thus, an implantable device that would continually and reliably measure blood-glucose concentration without requiring amperometric enzymatic biosensors would be very desirable. Moreover, as with any implantable device, there are attended risks associated with implanting the blood-glucose concentration monitor, such as adverse reactions to anesthetics employed during the implantation procedure or the onset of subsequent infections. Hence, it would be desirable to provide for automatic blood-glucose concentration monitoring using medical devices that would otherwise need to be implanted anyway, to thereby minimize the risks associated with the implantation of additional devices.

In view of the disadvantages of the state of the art with respect to glucose monitoring, it would be desirable to have a system that could painlessly measure blood-glucose concentration without drawing blood each time.

It would also be desirable to have a system that would automatically measure blood-glucose concentration of a patient without active user intervention.

It would further be desirable to have a system that would warn a diabetic before their blood-glucose concentration fell too low.

It would still further be desirable to have a system that could warn others if the diabetic's blood-glucose concentration fell low enough that they might be in diabetic shock.

It would yet further be desirable to have a system that could control delivery of insulin to a diabetic to better regulate their blood-glucose concentration.

It would yet further be desirable to have an implantable system that could measure glucose concentration without amperometric enzymatic biosensors.

SUMMARY OF INVENTION

In view of the background above and disadvantages of the state of the art, the present invention provides, in one embodiment, a method for calculating blood-glucose concentration using an implantable medical device implanted within a patient without the use of an amperometric enzymatic biosensor. The inventors have devised a metabolic oxygen conformation ("MOC") method which calculates blood-glucose concentration based upon its relationship to oxygen metabolism in the human body. The metabolic consumption of oxygen in the human body can be determined by measuring mixed venous oxygen concentration and cardiac output. Blood-glucose concentration is calculated based on the correlations between blood-glucose concentration and oxygen consumption along with other physiological variables such as heart-rate, blood flow, blood pressure and temperature. By using a combination of oxygen consumption and other variables, blood-glucose concentration can be reliably calculated throughout a wide range of concentrations. Once the blood-glucose concentration has been calculated, an implantable medical device compares the blood-glucose concentration against upper and lower acceptable bounds and appropriate warning signals are generated if the concentration falls outside the acceptable bounds. In one example, wherein an implantable insulin pump is additionally provided, the delivery of insulin is regulated in response to the calculated blood-glucose concentration to maintain blood-glucose concentration within an acceptable range.

In a specific embodiment, the implantable medical device is a pacemaker or implantable stimulation device. Hence, blood-glucose concentration monitoring is conveniently provided within patients already requiring a pacemaker or implantable stimulation device, without requiring implantation of additional devices. This combination is particularly useful because of the high comorbidity of diabetes and heart disease. Moreover, by using an implantable medical device to calculate blood-glucose concentration, no external monitoring device is required, no painful finger prick and no user intervention are needed. Hence, there is no risk the patient will fail to periodically measure blood-glucose concentration. Furthermore, blood-glucose concentration can be calculated as often as needed, for example, once every five minutes, allowing for more accurate control. Once the blood-glucose concentration has been calculated, the implantable medical device compares the blood-glucose concentration against acceptable upper and lower bounds and generates appropriate warning signals if the concentration is outside the acceptable bounds. If an implantable insulin pump or other therapeutic device is provided, the insulin pump or other therapeutic device may be automatically controlled in response to the calculated blood-glucose concentration to maintain the concentration within an acceptable range.

In a specific embodiment, a pacemaker or implantable stimulation device is provided with sensors to monitor cardiac output (by stroke volume and heart-rate), core and peripheral temperature (using implanted temperature sensors), mixed venous oxygen concentration (by venous oxygen saturation and hematocrit) and arterial oxygen concentration (by arterial oxygen saturation and hematocrit). Cardiac output can be determined using the pacemaker electrodes. Stroke volume can be calculated from the time variation of the bioimpedance between the tip of an intracardial electrode and the metallic housing of a pacemaker. The heart-rate is also monitored by the pacemaker. Cardiac output can then be calculated based on heart-rate and stroke volume. One or more implantable oxymeters are used to measure the oxygen concentration of mixed venous blood and the oxygen concentration in arterial blood. Using the cardiac output and the difference between the arterial and venous oxygen concentration, the metabolic oxygen consumption can be calculated by performing a Fick calculation: oxygen consumption=cardiac output*(arterial oxygen concentration−venous oxygen concentration). In the exemplary embodiment, the pacemaker or implantable stimulation device is provided with a control unit which utilizes the cardiac output, temperature, and blood-oxygen data in combination with stored information regarding the relationship of the cardiac output, temperature, and blood-oxygen data to blood-glucose concentration in accordance with the metabolic oxygen conformation method. By using a combination of oxymetric, temperature, and electrocardiographic data, blood-glucose concentration can be reliably calculated throughout a wide range of concentrations.

In accordance with a further aspect of the invention, a calibration technique is provided for determining patient-specific parameters for use in determining blood-glucose concentration. The calibration technique is implemented using an external programmer in communication with the implantable medical device. The programmer receives signals from the implantable medical device representative of internally-measured patient oxymetric, temperature, and electrocardiographic data. Simultaneously, the programmer receives data representative of the corresponding conventionally-measured patient blood-glucose concentrations. In a specific embodiment, blood-glucose concentrations are input from an external blood-glucose concentration monitor which measures blood-glucose concentration using otherwise conventional techniques such as the hexokinase method. The external blood-glucose concentration monitor is only employed during the calibration technique. To ensure that the parameters adequately represent a wide range of blood-glucose concentration, the parameters are calculated based on data accumulated while the blood-glucose concentration of the patient is caused to transition through a wide range of concentrations. More specifically, for non-insulin dependent patients, glucose is administered until the blood-glucose concentration rises to an upper threshold, such as 300 mg/dl, then insulin is administered until the blood-glucose concentration falls to a lower threshold, such as 40 mg/dl. For insulin-dependent patients, rather than administering glucose, it is sufficient to simply withhold insulin until the blood-glucose concentration has naturally risen to the upper threshold, then to administer insulin to reduce the blood-glucose concentration to the lower threshold. In either case, patient oxymetric, temperature, and electrocardiographic data are collected throughout the entire process. Using the data received from the implantable medical device and the conventionally-measured patient blood-glucose concentrations, the programmer derives patient-specific parameters that relate the patient's oxymetric, temperature, and electrocardiographic data to blood-glucose concentration in accordance with the metabolic oxygen conformation method. The patient-specific parameters are then transmitted to the implantable medical device such that the implantable medical device can thereafter calculate blood-glucose concentration from newly-measured patient oxymetric, temperature, and electrocardiographic data. In this manner, the blood-glucose concentration monitoring system of the implantable medical device is calibrated for the particular patient in whom the device is implanted. Alternatively or additionally, the device may be calibrated for a cluster of patients using regression analysis comparing conventionally-measured blood-glucose concentrations to the internally-measured variables across a population of patients.

In a specific embodiment, measures of mixed venous oxygen saturation, hematocrit and core temperature are obtained by an implantable stimulation device using an oxymeter and temperature sensor on a lead implanted in the right atrium. Cardiac output is monitored using cardiac electrodes in a conventional manner and blood pressure is monitored using a sensor implanted in the left atrium. Arterial oxygen concentration and peripheral temperature are obtained using a photoplethysmography sensor and temperature sensor mounted on the housing of the implantable stimulation device. The implantable stimulation device is calibrated for a user or cluster of users using regression analysis to compare conventionally-measured blood-glucose concentration to the internally-measured variables in accordance with the metabolic oxygen conformation method. The regression analysis yields a relationship function between the internally-measured variables and the blood-glucose concentration. The relationship function is then saved to the device or transmitted to a receiver ex vivo. The implantable device can then continuously monitor blood-glucose concentration based on new internally-measured variables.

Thus, various techniques are provided for monitoring blood-glucose concentration based on proxies of glucose metabolism derived from oxymetric, temperature, and electrocardiographic measurements using an implantable device and for calibrating the implantable device for use with individual patients. The monitoring and control of glucose concentrations facilitated by the invention is beneficial to diabetics as well as subjects who have not been diagnosed as diabetic. Other objects, features and advantages of the invention will be apparent from the detailed description to follow.

BRIEF DESCRIPTION OF THE DRAWINGS

The above and further features, advantages and benefits of the present invention will be apparent upon consideration of the present description taken in conjunction with the accompanying drawings, in which:

FIG. 6A shows an exemplary oxymeter suitable for use in the implantable stimulation device of FIGS. 1 and 2;

FIG. 6B shows an exemplary photoplethysmography sensor for use in the implantable stimulation device of FIGS. 1 and 2;

FIG. 6C shows a sectional view of the photoplethysmography sensor of FIG. 6B.

DETAILED DESCRIPTION

Figure 1:
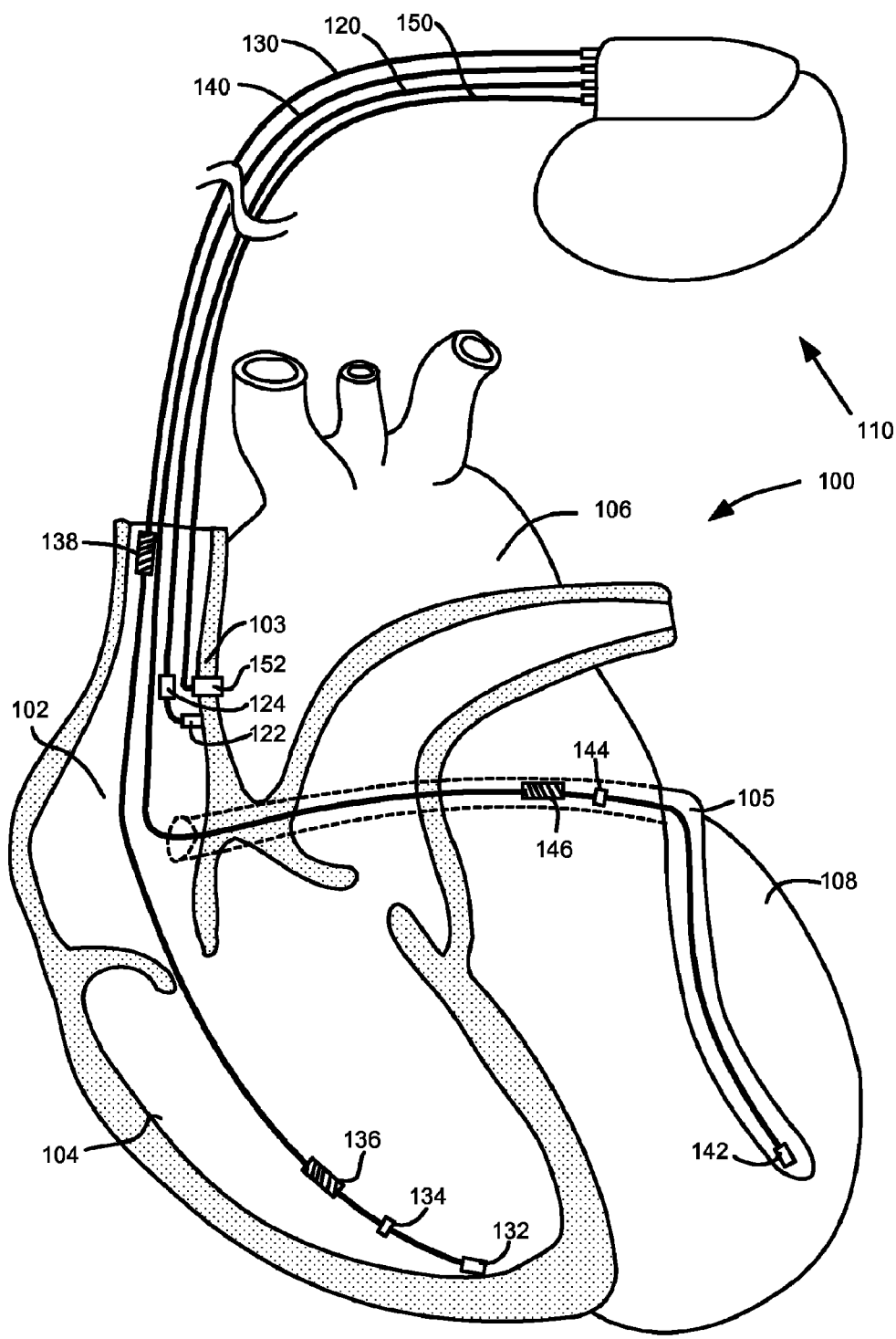
FIG. 1 is a simplified, partly cutaway view illustrating an implantable stimulation device in electrical communication with at least three leads implanted into a patient's heart for delivering multi-chamber stimulation and shock therapy.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the left-most digit of a reference number identifies the drawing in which the reference number first appears.

Implantable Stimulation Device

FIG. 1 illustrates an exemplary implantable stimulation device 110 in electrical communication with a patient's heart 100 by way of three leads 120, 130, 140 and 150 suitable for multi-chamber sensing, stimulation and shock therapy. To sense atrial cardiac signals and to provide right atrial chamber stimulation therapy, implantable stimulation device 110 is coupled to an implantable right atrial lead 120 having at least an atrial tip electrode 122, which typically is implanted in the patient's right atrial appendage. In accordance with one embodiment of the present invention, right atrial lead 120 also comprises an oxymeter 124 for measuring mixed-venous oxygen saturation.

To sense left atrial and ventricular cardiac signals and to provide left-chamber pacing therapy, implantable stimulation device 110 is coupled to a "coronary sinus" lead 140 designed for placement in the "coronary sinus region" 105 via the coronary sinus so as to place a distal electrode adjacent to the left ventricle 108 and additional electrode(s) adjacent to the left atrium 106. As used herein, the phrase "coronary sinus region" 105 refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 140 is designed to receive atrial and ventricular cardiac signals and to deliver left ventricular pacing therapy using at least a left ventricular tip electrode 142, left atrial pacing therapy using at least a left atrial ring electrode 144, and shocking therapy using at least a left atrial coil electrode 146.

Implantable stimulation device 110 is also shown in communication with the patient's heart 100 by way of an implantable left atrial lead 150 having in this embodiment, a left atrial sensor 152 implanted in the septum 103 between the right atrium 102 and left atrium 106. Left atrial sensor 152 is in one embodiment comprises a hermetically-sealed pressure transducer module. In one embodiment, the implantable module comprises a proximal anchor and a distal anchor which are configured to sandwich an atrial septum wall 103 (or the left atrial free wall, the pulmonary vein wall, or any other suitable wall of a heart or a blood vessel) between the proximal anchor leg and the distal anchor leg and to support the module in the septum wall 103. In one embodiment, the sensor module comprises one or more sensors in addition to a pressure transducer at its distal end. These sensors may include a plurality of pressure transducers to measure pressures in the transmural space or locations proximal to the transmural space, or to measure differential pressure between the distal diaphragm and another location. Other types of sensors include, but are not limited to, temperature sensors, electrodes for measuring electrical activity, and oxymeters. In one embodiment, the sensor module contains at least one electrode for stimulating the organ in which it is placed. For example, such an electrode or electrodes may be used for electrical pacing the left atrium. A suitable embodiment of a lead-mounted left atrial sensor is the Savacor HEARTPOD™ which in the present application is connected via lead 150 to implantable stimulation device 110. Details of such left atrial sensor modules may be found in U.S. patent application Ser. No. 11/115,991 entitled, "Implantable Pressure Transducer System Optimized For Anchoring And Positioning" filed Apr. 27, 2005 to Eigler et al.; Ser. No. 10/270,784 entitled "Permanently Implantable System And Method For Detecting, Diagnosing And Treating Congestive Heart Failure" filed: Oct. 11, 2002 to Eigler et al.; and Ser. No. 11/027,598 entitled "Flexible Lead For Digital Cardiac Rhythm Management" filed: Dec. 30, 2004 to Mann et al. all of which are incorporated herein by reference.

Implantable stimulation device 110 is also shown in electrical communication with the patient's heart 100 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 100 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals, and delivering stimulation in the form of pacing and shock therapy to the right ventricle. In accordance with one embodiment of the present invention, the time-varying impedance between an electrode in the right ventricle and the body of implantable stimulation device 110 is used to calculate cardiac stroke volume.

Figure 2:
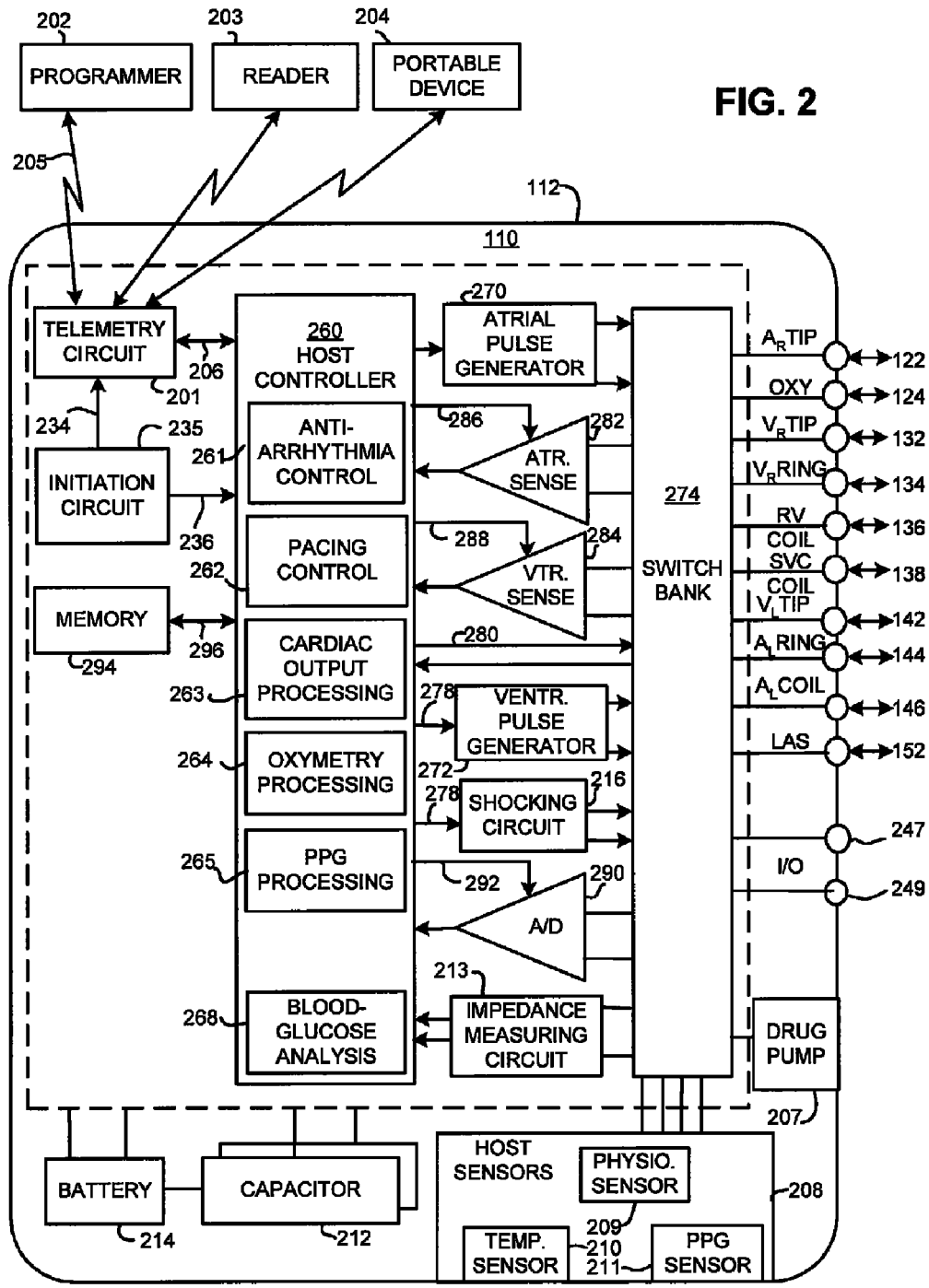
FIG. 2 is a functional block diagram of the multi-chamber implantable stimulation device of FIG. 1, illustrating the basic elements that provide cardioversion, defibrillation and/or pacing stimulation in four chambers of the heart and illustrating a blood-glucose concentration monitoring unit for automatically calculating blood-glucose concentration from oxymetric, temperature, and electrocardiographic measurements in accordance with specific embodiments of the present invention.

FIG. 2 illustrates a simplified block diagram of the multi-chamber implantable stimulation device 110 which is capable of measuring blood-glucose concentration and treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of measuring blood-glucose concentration with or without treating the heart with cardioversion, defibrillation and/or pacing stimulation.

Referring again to FIG. 2, implantable stimulation device 110 includes a housing 112 which is often referred to as a "can", "case" or "case electrode", and which may be programmably selected to act as the return electrode for all "unipolar" modes. Housing 112 may further be used as a return electrode alone or in combination with one or more of the coil electrodes 146, 136, or 138, for shocking purposes. Housing 112 further includes a connector (not shown) having a plurality of terminals, 242, 243, 244, 245, 246, 247, 248, 249, 252, 254, 256, and 258 (shown schematically and, for convenience, the names of the electrodes to which they are connected are shown next to the terminals). To achieve right atrial sensing and pacing, the connector includes at least a right atrial tip terminal 242 adapted for connection to the right atrial (AR) tip electrode 122, a right atrial oxymeter terminal 243 adapted for connection to the oxymeter 124. To achieve left chamber sensing, pacing and/or shocking, the connector includes at least a left ventricular (VL) tip terminal 244, a left atrial sensor terminal, 245, a left atrial (AL) ring terminal 246, and a left atrial (AL) shocking terminal (coil) 248, which are adapted for connection to the left ventricular tip electrode 142, the left atrial sensor 152, the left atrial ring electrode 144, and the left atrial coil electrode 146, respectively. To support right chamber sensing, pacing and/or shocking, the connector further includes a right ventricular (VR) tip terminal 252, a right ventricular (VR) ring terminal 254, a right ventricular (RV) shocking terminal (coil) 256, and an SVC shocking terminal (coil) 258, which are adapted for connection to the right ventricular tip electrode 132, right ventricular ring electrode 134, the RV coil electrode 136, and the SVC coil electrode 138, respectively. The connector may also include one or more I/O terminals 247, 249 for communicating with optional implantable devices external to housing 112.

At the core of implantable stimulation device 110 is a programmable host controller 260 which controls the various modes of stimulation therapy and performs calculations of blood-glucose concentration. As is well known in the art, host controller 260 may be a microcontroller and typically includes a microprocessor or equivalent control circuitry or processor, designed specifically for controlling the delivery of stimulation therapy, and may further include RAM or ROM memory, logic and timing circuitry, state machine circuitry, and I/O circuitry. Typically, host controller 260 includes the ability to process or monitor input signals (data) as controlled by program code stored in a designated block of memory. Host controller 260 includes the ability to calculate blood-glucose concentration from measured oxymetric, temperature, and electrocardiographic variables and stored parameters. The details of the design and operation of host controller 260 are not critical to the present invention. Rather, any suitable host controller 260 may be used that carries out the functions described herein. The use of microprocessor-based control circuits for performing timing and data analysis functions is well known in the art.

As shown in FIG. 2, an atrial pulse generator 270 and a ventricular pulse generator 272 generate pacing stimulation pulses for delivery by right atrial lead 120, right ventricular lead 130, and/or coronary sinus lead 140 via a switch bank 274. It is understood that in order to provide stimulation therapy in each of the four chambers of the heart, atrial pulse generator 270 and ventricular pulse generator 272 may include dedicated, independent pulse generators, multiplexed pulse generators, or shared pulse generators. Atrial pulse generator 270 and ventricular pulse generator 272 are controlled by host controller 260 via appropriate control signals 276 and 278, respectively, to trigger or inhibit the stimulation pulses.

Host controller 260 further includes pacing control circuitry 262 which is used to control the timing of such stimulation pulses (e.g., pacing rate, atrio-ventricular (A-V) delay, atrial interconduction (A-A) delay, ventricular interconduction (V-V) delay, pacing mode, etc.), as well as to keep track of the timing of refractory periods, PVARP intervals, noise detection windows, evoked response windows, alert intervals, marker channel timing, etc.

Implantable stimulation device 110 may operate as an implantable cardioverter/defibrillator (ICD) device. That is, it may detect the occurrence of an arrhythmia, and automatically apply an appropriate electrical shock therapy to the heart aimed at terminating the detected arrhythmia. To this end, host controller 260 further controls a shocking circuit 216 by way of a control signal 218. The shocking circuit 216 generates shocking pulses of low (up to 0.5 joules), moderate (0.5-10 joules), or high (11-40 joules) energy, as controlled by the host controller 260. Such shocking pulses are applied to the patient's heart through at least two shocking electrodes, as shown in this embodiment, selected from left atrial coil electrode 146, RV coil electrode 136, and/or SVC coil electrode 138 (FIG. 1). As noted above, housing 112 may act as an active electrode in combination with the RV electrode 136, or as part of a split electrical vector using SVC coil electrode 138 or left atrial coil electrode 146 (e.g., using the RV electrode as a common electrode).

Switch bank 274 includes a plurality of electrically-configurable switches for connecting the desired electrodes to the appropriate I/O circuits, thereby providing complete electrode programmability. Accordingly, switch bank 274, in response to a control signal 280 from host controller 260, determines the polarity of the stimulation pulses (e.g., unipolar, bipolar, combipolar, etc.) by selectively closing the appropriate combination of switches (not shown) as is known in the art. If multiple RV electrodes are employed to generate a single averaged ventricular signal, then switch bank 274 is configured to allow the paralleling (or averaging) of the multiple RV electrodes to simulate a large electrode for accurate sensing of the T-wave.

Atrial sensing circuits 282 and ventricular sensing circuits 284 may also be selectively coupled to right atrial lead 120, coronary sinus lead 140, and right ventricular lead 130, through the switch bank 274, for detecting the presence of cardiac activity in each of the four chambers of the heart. Accordingly, the atrial and ventricular sensing circuits 282 and 284 may include dedicated sense amplifiers, multiplexed amplifiers, or shared amplifiers. Switch bank 274 determines the "sensing polarity" of the cardiac signal by selectively closing the appropriate switches. In this way, the clinician may program the sensing polarity independent of the stimulation polarity.

Each of the sensing circuits, 282 and 284, preferably employ one or more low power, precision amplifiers with programmable gain and/or automatic gain control, bandpass filtering, and a threshold detection circuit, to selectively sense the cardiac signal of interest. The automatic gain control enables implantable stimulation device 110 to deal effectively with the difficult problem of sensing the low amplitude signal characteristics of atrial or ventricular fibrillation.

The outputs of the atrial and ventricular sensing circuits 282 and 284 are connected to host controller 260 for triggering or inhibiting the atrial and ventricular pulse generators 270 and 272, respectively, in a demand fashion, in response to the absence or presence of cardiac activity, respectively, in the appropriate chambers of the heart. The atrial and ventricular sensing circuits 282 and 284, in turn, receive control signals over signal lines 286 and 288 from host controller 260, for controlling the gain, threshold, polarization charge removal circuitry (not shown), and the timing of any blocking circuitry (not shown) coupled to the inputs of the atrial and ventricular sensing circuits 282 and 284.

For arrhythmia detection, implantable stimulation device 110 utilizes the atrial and ventricular sensing circuits 282 and 284 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the host controller 260 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition unit 290. Data acquisition unit 290 is configured to acquire intracardiac electrogram signals, convert the raw analog data into digital signals, and store the digital signals for later processing and/or telemetric transmission to an external device 202. Data acquisition unit 290 is coupled to right atrial lead 120, the coronary sinus lead 140, the right ventricular lead 130, and the left atrial lead 150 through the switch bank 274 to sample cardiac signals across any pair of desired electrodes.

Advantageously, data acquisition unit 290 may be coupled to host controller 260 or other detection circuitry, for detecting an evoked response from the heart 100 in response to an applied stimulus, thereby aiding in the detection of "capture". Capture occurs when an electrical stimulus applied to the heart is of sufficient energy to depolarize the cardiac tissue, thereby causing the heart muscle to contract. Host controller 260 detects a depolarization signal during a window following a stimulation pulse, the presence of which indicates that capture has occurred. Host controller 260 enables capture detection by triggering the ventricular pulse generator 272 to generate a stimulation pulse, starting a capture detection window using the timing circuitry within host controller 260, and enabling data acquisition unit 290 via control signal 292 to sample the cardiac signal that falls in the capture detection window and, based on the amplitude of the sampled cardiac signal, determines if capture has occurred. The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection unit used is not critical to the present invention.

Implantable stimulation device 110 may also include one or more host sensors 208, which can be located within the housing 112 of implantable stimulation device 110 as shown, or can be located external to the housing. These sensors can include, by way of example, blood flow sensors, temperature sensors, and blood pressure sensors. Host sensors 208 may include a physiologic sensor 209, a temperature sensor 210 and a PPG sensor 211. As shown in FIG. 2, host sensors 208 may be connected to via switch bank 274 to host controller 260 directly or through data acquisition unit 290 such that host controller 260 can receive measurements of the physiological variables from the host sensors 208.

Physiologic sensor 209 is commonly referred to as a "rate-responsive" sensor because it is typically used to adjust pacing stimulation rate according to the exercise state of the patient. However, the rate-responsive sensor may also be used to detect changes in cardiac output, changes in the physiological condition of the heart, or diurnal changes in activity (e.g., detecting sleep and wake states). Accordingly, host controller 260 responds to the rate-responsive sensor by adjusting the various pacing parameters (such as rate, AV Delay, V-V Delay, etc.) at which the atrial and ventricular pulse generators, 270 and 272, generate stimulation pulses.

Temperature sensor 210 may comprise any electronic device for measuring temperature. Suitable devices include, but are not limited to, thermopiles, thermistors, thermocouples. Thermopiles measure temperature by measuring IR radiation incident of the detector surface. Thus, if a thermopile is used as temperature sensor 210, a window transparent to IR (not shown) must be provided to allow heat/IR radiation from the blood to fall on the surface of the detector. Thermistors and thermocouples may measure temperature by conduction. Such temperature measuring devices should therefore be placed in good thermal contact with the blood. As shown in FIG. 2, temperature sensor 210 may be placed in contact with housing 112 of implantable stimulation device 110. Housing 112 is preferably made of metal. As housing 112 is in good thermal contact with the tissues surrounding the housing and also with temperature sensor 210, and because metal is a good conductor of heat, temperature sensor 210 can accurately measure the temperature of the body at the location where implantable stimulation device 110 has been implanted. Preferably implantable stimulation device 110 is implanted in the subclavian pocket and thus temperature sensor 210 measures the temperature of the body in the subclavian pocket. This temperature will vary based on such factors as external temperature and activity of the subject.

PPG Sensor 211 comprises a photoplethysmography sensor which may be used to measure oxygen saturation in the tissues adjacent the housing 112. PPG Sensor 211 comprises a number of light sources of different wavelengths and a light detector. The light detector detects light from the light sources which is reflected back from the tissues next to PPG sensor 211. Preferably implantable stimulation device 110 is implanted in the subclavian pocket and thus PPG sensor 210 may be used to measure the oxygen saturation level in the tissues of the subclavian pocket using pulse oximetry techniques as will be described in more detail with respect to FIGS. 6B-C. The oxygen saturation level in the tissues of the subclavian pocket as measured by PPG sensor 211 can be used as a measure of arterial oxygen saturation.

As further shown in FIG. 2, implantable stimulation device 110 comprises an impedance measuring circuit 213 which is enabled by host controller 260 via a control signal 214. Certain applications for an impedance measuring circuit 213 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. Impedance measuring circuit 213 is advantageously coupled to the switch bank 274 so that any desired electrode may be used.

Host controller 260 is also coupled to a memory 294 by a suitable data/address bus 296. Memory 294 stores the programmable operating parameters used by the host controller 260 in order to customize the operation of implantable stimulation device 110 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 100 within each respective tier of therapy. A feature of implantable stimulation device 110 is the ability to receive and store a relatively large amount of data (e.g., from data acquisition unit 290), which data may then be used for subsequent analysis to guide the programming of implantable stimulation device 110.

Advantageously, the operating parameters of the implantable device 110 may be non-invasively programmed into the memory 294 through a telemetry circuit 201 in telemetric communication with an external programmer 202, such as a, transtelephonic transceiver, or a diagnostic system analyzer. The telemetry circuit 201 is activated by the host controller by a control signal 206. The telemetry circuit 201 advantageously allows intracardiac electrograms, blood-glucose concentration results, oxygen saturation information, temperature data, hematocrit information, stroke volume, heart-rate, other measured physiological variable and status information relating to the operation of the implantable stimulation device 110 (as contained in the host controller 260 or memory 294) to be sent to an external device such as programmer 202, reader 203, or portable device 204 through an established communication link 205. Typically the communication link can only operate between telemetry circuit 201 and one of programmer 202, reader 203, or portable device 204 at any one time. A "handshake" signal sent from the external device may be used to identify the particular device with which the telemetry circuit 201 is in communication thereby defining what operations may be performed by the device. For example, programming of implantable stimulation device 110 will preferably only be permitted by programmer 202 under the control of a physician.

Implantable stimulation device 110 further includes initiation circuit 235. Initiation circuit 235 may comprise magnet detection circuitry. Initiation circuit 235 is coupled to host controller 260 by connection 236 and/or to telemetry circuit 201 by connection 234. The purpose of the initiation circuit is to detect an initiation signal from outside the patient. For example, a magnet placed over the cardiac implantable stimulation device 110 may be used as the initiation signal, which magnet may be used by a clinician to perform various test functions of the cardiac implantable stimulation device 110 and/or to signal host controller 260 that an external programmer 202 is in place to receive or transmit data to host controller 260 through the telemetry circuit 201. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275, 734, entitled "Efficient Generation of Sensing Signals in an Implantable Medical Device such as a Pacemaker or ICD" (note: this relates to transfer of EGM data) (McClure et al.), which patents are hereby incorporated herein by reference.

In an embodiment of the invention, a blood-glucose analysis unit 268 of host controller 260 processes signals representative of heart-rate, stroke volume, arterial oxygen saturation, hematocrit, blood flow, blood pressure, venous oxygen saturation and temperature, or sub-combinations thereof. Oxymetry processing unit 264 calculates oxygen saturation and hematocrit information from the outputs of an oxymeter 124 (See FIG. 1). PPG processing unit calculates oxygen saturation fro the output of the PPG sensor 211. Cardiac output processing unit 263 determines cardiac output from measures of stroke volume and heart-rate using electrocardiographic and bioimpedance data. Blood-glucose analysis unit 268 calculates the current blood-glucose concentration within the bloodstream of the patient from the oxymetric, temperature, and electrocardiographic data in combination with parameters stored in memory 294. The operation of blood-glucose analysis 268 unit is described in detail below with reference to FIG. 5.

If an insulin pump 207 is provided, blood-glucose analysis unit 268 transmits control signals to insulin pump 207 for adjusting the amount of insulin delivered to the patient in response to the current blood-glucose concentration. Information regarding implantable insulin pumps may be found in U.S. Pat. No. 4,731,051 to Fischell and in U.S. Pat. No. 4,947,845 to Davis, both of which are incorporated by reference herein. The insulin pumps discussed therein, or other suitable insulin pumps, are modified as needed to permit receipt of control signals from blood-glucose analysis unit 268. Blood-glucose analysis unit 268 can likewise be used to control other implantable therapeutic devices which can be used to affect blood-glucose concentration. For example, it has been suggested that stimulation of the autonomic nerves innervating the pancreas may be used to control insulin secretion. This stimulation could be achieved using properly placed electrodes connected to terminals of implantable stimulation device 110. The stimulation may be adjusted in response to control signals from blood-glucose analysis unit 268 thereby affecting the amount of insulin secreted by the pancreas in response to the calculated blood-glucose level.

Implantable stimulation device 110 additionally includes a power source such as a battery 214 which provides operating power to all the circuits of implantable stimulation device 110. For implantable stimulation device 110, which employs shocking therapy, battery 214 must be capable of operating at low current drains for long periods of time and also be capable of providing high-current pulses (for charging capacitor 212) when the patient requires a shock pulse. Battery 214 preferably has a predictable discharge characteristic so that elective replacement time can be detected. Accordingly, implantable stimulation device 110 can employ lithium/silver vanadium oxide batteries.

Programmer

Figure 3:
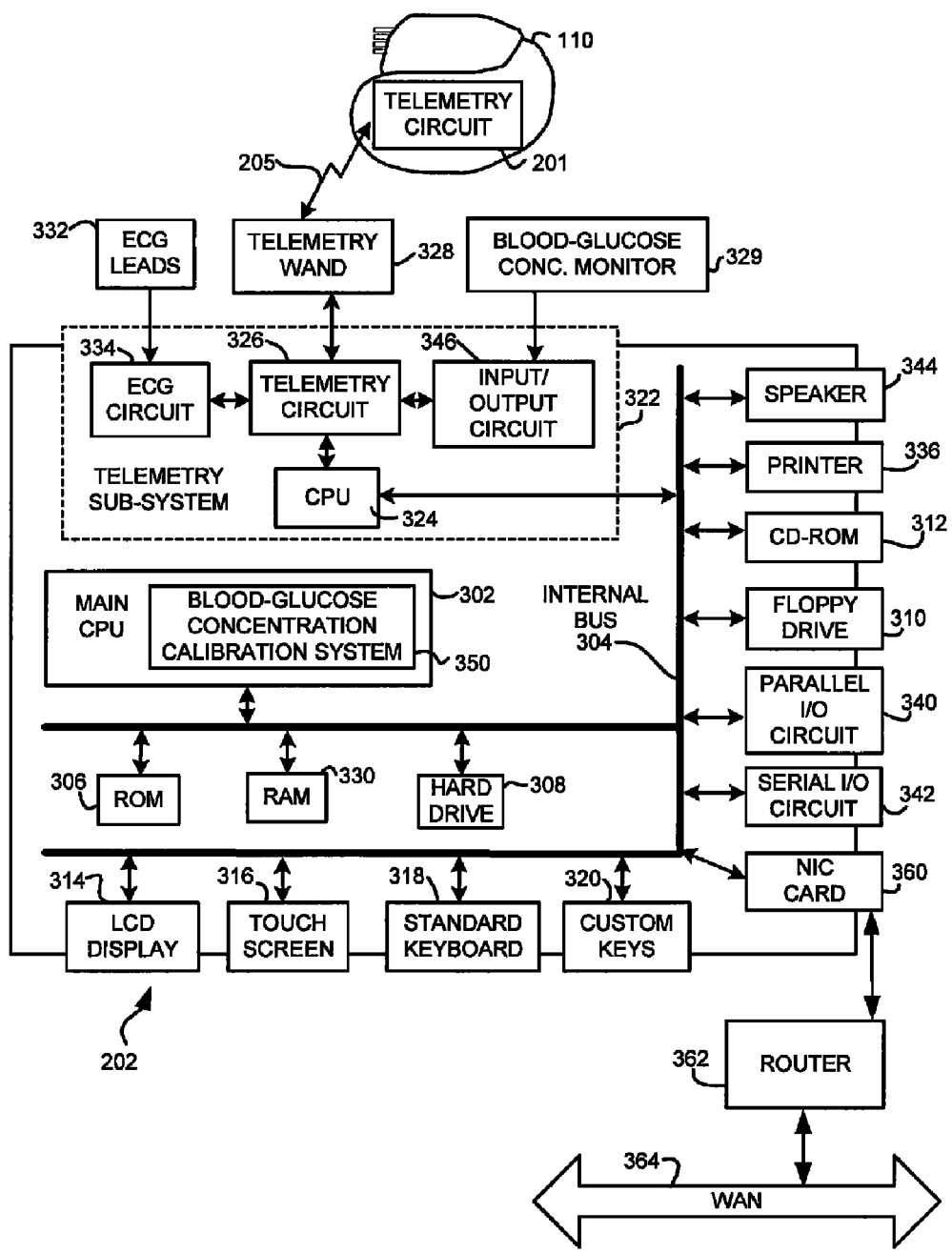
FIG. 3 is a functional block diagram illustrating components of a programmer for use in programming the implantable device of FIGS. 1 and 2, and in particular illustrating a calibration system for use in calibrating the blood-glucose concentration monitoring unit of the implantable device in accordance with specific embodiments of the present invention.

FIG. 3 illustrates pertinent components of programmer 202 for use in programming an implantable medical device for determining blood-glucose concentration utilizing the metabolic oxygen concentration method. Programmer 202 permits a physician or other user to program the operation of the implantable stimulation device 110 and to retrieve and display information received from the implantable stimulation device 110 such as stroke volume, heart-rate, oxymetry data, PPG data, blood-glucose concentration data, measured physiological variables data, EGM data and device diagnostic data. Additionally, programmer 202 may receive and display ECG data from separate external ECG leads that may be attached to the patient. Programmer 202 may also be capable of processing and analyzing data received from the implantable stimulation device 110 and from the ECG leads 332 to, for example, render preliminary diagnosis of medical conditions of the patient or the operations of the implantable stimulation device 110.

Operations of programmer 202 are controlled by a CPU 302, which may be a generally programmable microprocessor or microcontroller or may be a dedicated processing device such as an application specific integrated circuit (ASIC) or the like. Software instructions to be performed by the CPU are accessed via an internal bus 304 from a read only memory (ROM) 306 and random access memory 330. Additional software may be accessed from a hard drive 308, floppy drive 310, and CD ROM 312, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 314 or other suitable computer display device. To this end, the CPU may, for example, display a menu of specific programming parameters of the implantable stimulation device 110 to be programmed or may display a menu of types of diagnostic data to be retrieved and displayed. In response thereto, the physician enters various commands via either a touch screen 316 overlaid on the LCD display 314 or through a standard keyboard 318 supplemented by additional custom keys 320, such as an emergency VVI (EVVI) key. The EVVI key sets the implantable stimulation device 110 to a safe VVI mode with high pacing outputs. This ensures life sustaining pacing operation in nearly all situations but by no means is it desirable to leave the implantable device in the EVVI mode at all times.

Typically, the physician initially controls programmer 202 to retrieve data stored within the implanted medical device and to also retrieve ECG data from ECG leads 332, if any, coupled to the patient. To this end, CPU 302 transmits appropriate signals to a telemetry subsystem 322, which provides components for directly interfacing with the implantable stimulation device 110, the blood-glucose monitor 329 and the ECG leads 332. Telemetry subsystem 322 includes its own separate CPU 324 for coordinating the operations of the telemetry subsystem. Main CPU 302 of programmer 202 communicates with telemetry subsystem CPU 324 via internal bus 304. Telemetry subsystem 322 includes a telemetry circuit 326 connected to a telemetry wand 328, which, in turn, receives and transmits signals electromagnetically from a telemetry circuit 201 of a implantable stimulation device 110. Telemetry wand 328 is placed over the chest of the patient near the implantable stimulation device 110 to permit reliable transmission of data between the telemetry wand and the implantable stimulation device 110. Typically, at the beginning of the programming session, programmer 202 controls the implantable stimulation device 110 via appropriate signals generated by telemetry wand 328 to output all previously recorded patient and device diagnostic information. Patient diagnostic information includes, for example, stroke volume, heart-rate, oxymetry data, PPG data, blood-glucose concentration data, measured physiological variables data, recorded EGM data and statistical patient data such as the percentage of paced versus sensed heartbeats. Device diagnostic data includes, for example, information representative of the operation of the implantable stimulation device 110 such as lead impedances, battery voltages, battery recommended replacement time (RRT) information and the like. Data retrieved from the implantable stimulation device 110 is stored by programmer 202 either within a random access memory (RAM) 330, hard drive 308 or within a floppy diskette placed within floppy drive 310. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implantable stimulation device 110 is transferred to programmer 202, the implantable stimulation device 110 may be further controlled to transmit additional data in real time as it is measured by the implantable stimulation device 110, such as additional stroke volume, heart-rate, oxymetry data, PPG data, blood-glucose concentration data, measured physiological variables data, EGM data, lead impedance data, and the like. Telemetry subsystem 322 may include input/output circuit 346 for communicating with external blood-glucose monitor 329.

Telemetry subsystem 322 is connected to blood-glucose monitor 329 by input/output circuit 346. Blood-glucose monitor 329 is a conventional external blood-glucose monitor which monitors the concentration of glucose in samples of the patient's blood using standard methods such as the hexokinase method. Additionally, telemetry subsystem 322 may receive ECG signals from ECG leads 332 via an ECG circuit 334. As with data retrieved from the implantable stimulation device 110, signals received from the ECG leads 332 and blood-glucose monitor 329 are stored within one or more of the storage devices of the external programmer. Typically, ECG leads output analog electrical signals representative of the ECG. Accordingly, ECG circuit 334 includes analog to digital conversion circuitry for converting the signals to digital data appropriate for further processing within programmer. Depending upon the implementation, the ECG circuit may be configured to convert the analog signals into event-record data for ease of processing along with the event-record data retrieved from the implantable stimulation device 110. Typically, signals received from the ECG leads 332 and blood-glucose monitor 329 are received and processed in real time.

Thus, programmer 202 receives data both from the implantable stimulation device 110 and from the external ECG leads and blood-glucose monitor. Data retrieved from the implantable stimulation device 110 includes parameters representative of the current programming state of the implantable stimulation device 110. Under the control of the physician, programmer 202 displays the current programming parameters and permits the physician to reprogram the parameters. To this end, the physician enters appropriate commands via any of the aforementioned input devices and, under control of CPU 302, the programming commands are converted to specific programming parameters for transmission to the implantable stimulation device 110 via telemetry wand 328 to thereby reprogram the implantable stimulation device 110. Prior to reprogramming specific parameters, the physician may control the programmer 202 to display any or all of the data retrieved from the implantable stimulation device 110 or from the ECG leads, including displays of ECGs, EGMs, and statistical patient information. Any or all of the information displayed by programmer may also be printed using a printer 336.

CPU 302 includes a blood-glucose concentration calibration unit 350 for generating patient-specific parameters for transmission to implantable stimulation device 110. Data for the operation of the blood-glucose concentration calibration unit 350 is derived from measurements of stroke volume, heart-rate, oxymetry data and other measured physiological variables transmitted from implantable device 110 via telemetry wand 328 in addition to the data recorded by blood-glucose monitor 329. The operation of blood-glucose concentration calibration unit 350 is described in detail below primarily with reference to FIG. 5.

Programmer 202 also includes a network interface card ("NIC") 360 to permit transmission of data to and from other computer systems via a router 362 and wide area network ("WAN") 364. Alternatively, programmer 202 might include a modem for communication via the public switched telephone network (PSTN). Depending upon the implementation, a modem may be connected directly to internal bus 304 may be connected to the internal bus via either a parallel port 340 or a serial port 342. Other peripheral devices (such as the blood-glucose monitor) may be connected to the programmer 202 via parallel port 340 or a serial port 342 as well. Although one of each is shown, a plurality of input output (10) ports might be provided.

A speaker 344 is included for providing audible tones to the user, such as a warning beep in the event improper input is provided by the physician. Telemetry subsystem 322 additionally includes an input/output circuit 346 which can control the transmission of analog output signals, such as EGM signals output to an ECG machine or chart recorder.

With the programmer configured as shown, a physician or other user operating the programmer 202 is capable of retrieving, processing and displaying a wide range of information received from the ECG leads or from the implantable stimulation device 110 and to reprogram the implantable stimulation device 110 if needed. The descriptions provided herein with respect to FIG. 3 are intended merely to provide an overview of the operation of programmer and are not intended to describe in detail every feature of the hardware and software of the device and are not intended to provide an exhaustive list of the functions performed by the device.

Glucose Concentration Analysis Using the Metabolic Oxygen Conformation Method

The metabolic oxygen conformation method allows for calculation of blood-glucose concentration without the use of amperometric enzymatic biosensors. Blood-glucose concentration may be monitored by monitoring physiological variables that relate to glucose metabolism and deriving parameters that relate those variables to the concentration of glucose in the blood. The metabolism of glucose is the primary use of oxygen in the human body. Thus, in the metabolic oxygen conformation method, oxygen metabolism is used as a proxy for glucose metabolism. The following conceptual equation indicates the relationship between blood-glucose concentration and physiological variables related to oxygen metabolism:

G=F (oxygen consumption, blood flow, oxygen concentration, temperature)

"G" represents the concentration of glucose in the blood and "F" is a relationship function between a set of interdependent and correlated metabolic variables related to oxygen metabolism (as a proxy for glucose metabolism). The parameters of the relationship function "F" may be determined by using multivariate statistical techniques to compare the conventionally-measured blood-glucose concentrations to the measured metabolic variables over a range of different blood-glucose concentrations in a specific patient or in clusters of patients within a population. In one embodiment of the invention, the relationship function "F" is determined using regression analysis. When determining the relationship function between the measured variables and the blood-glucose concentration, linear relationships are preferred because they are simple to calculate and may provide an adequate equation for deriving the blood-glucose concentration of the patient. However, other mathematical relationships can instead be employed, including nonlinear equations.

Different combinations of variables may be monitored in order to create an accurate set of parameters to determine blood-glucose concentration in accordance with the conceptual equation of the metabolic oxygen conformation method. For example, oxygen consumption can be calculated by the Fick formula: oxygen consumption=cardiac output*(arterial oxygen concentration−venous oxygen concentration). Cardiac output can be calculated by stroke volume*heart-rate. Stroke volume may be determined by analysis of the time-varying impedance between an intracardiac electrode and the housing 112 of implantable stimulation device 110. Blood flow may be measured directly, or may be inferred from cardiac output (or cardiac output in combination with blood pressure). Thus, rather than using oxygen consumption as a variable, related variables can be used instead, namely: stroke volume, heart-rate, venous oxygen concentration, and arterial oxygen concentration. Likewise, rather than using venous oxygen concentration as a variable in the regression analysis, its sub-variables, venous oxygen saturation and hematocrit may be used instead. Temperature can be measured in the core and in peripheral tissues and will vary depending on activity levels and blood flow distributions. Referring again to the conceptual equation and making substitutions with the measured variables:

G=F (oxygen consumption, blood flow, oxygen concentration, temperature)

Oxygen consumption=f (stroke volume, heart rate, venous oxygen concentration, arterial oxygen concentration)

Tissue blood flow=f (stroke volume, heart rate, blood pressure)

Tissue oxygen concentration=f (venous oxygen concentration, arterial oxygen concentration, blood flow)

Venous oxygen concentration=f (hematocrit, venous oxygen saturation)

Arterial oxygen concentration=f (hematocrit, arterial oxygen saturation)

Thus, G=F (stroke volume, heart-rate, hematocrit, venous oxygen saturation, arterial oxygen saturation, blood pressure, core temperature, peripheral temperature).

Other variables that relate to glucose or oxygen metabolism may be added if needed to improve the accuracy of the blood-glucose concentration determination, for example, blood pressure measured in the core and peripheral tissues, blood flow measured by a discrete flow meter (such as a Doppler flow meter). Blood pressure may be a useful variable in order to deal with varying blood flow distributions in various body conditions. For example, vasodilation usually leads to high peripheral blood flow, and lower blood pressure for the same cardiac output. Whereas vasoconstriction leads to low peripheral blood flow and higher blood pressure for the same cardiac output. Hematocrit and venous and arterial oxygen concentration may be measured by an oxymeter or PPG sensor as described with reference to FIGS. 6A-C below.

In principle, regression analysis models the relationship between one or more response variables (also called dependent variables), and the predictors (also called independent variables). Simple linear regression and multiple linear regression are related statistical methods for modeling the relationship between two or more random variables using a linear equation. Simple linear regression refers to a regression on two variables while multiple regression refers to a regression on more than two variables. Regression analysis can be used to determine the parameters of the relationship between the variables of the conceptual equation of the Metabolic Oxygen Conformation Method. In order to perform the regression analysis, data must be collected regarding the variables over a wide range of conditions as will be described with respect to FIGS. 4 and 5. During the regression analysis of the measured variables compared to actual blood-glucose concentration the measured variables necessary for an accurate blood-glucose concentration determination may be selected and others may be found unnecessary and dropped from later calculations. Thus, regression analysis may show that measurement of certain variables is not required in some individuals or clusters of individuals but is required in other individuals and clusters of individuals. The regression analysis generates parameters which specify which variables are required to be measured and the relationship of those variables to the subjects' blood-glucose concentration. Depending on the individual or cluster of individuals and the accuracy with to which glucose concentration is required regression analysis of the data may demonstrate the following combinations of physiological metrics, for example, to be sufficient to calculate glucose concentration: venous oxygen saturation; venous oxygen saturation and temperature; venous oxygen saturation and hematocrit; venous oxygen saturation, temperature and heart-rate; venous oxygen saturation and blood pressure; venous oxygen saturation, blood pressure and heart-rate; hematocrit and temperature; and hematocrit, blood pressure and heart rate.

Figure 4:
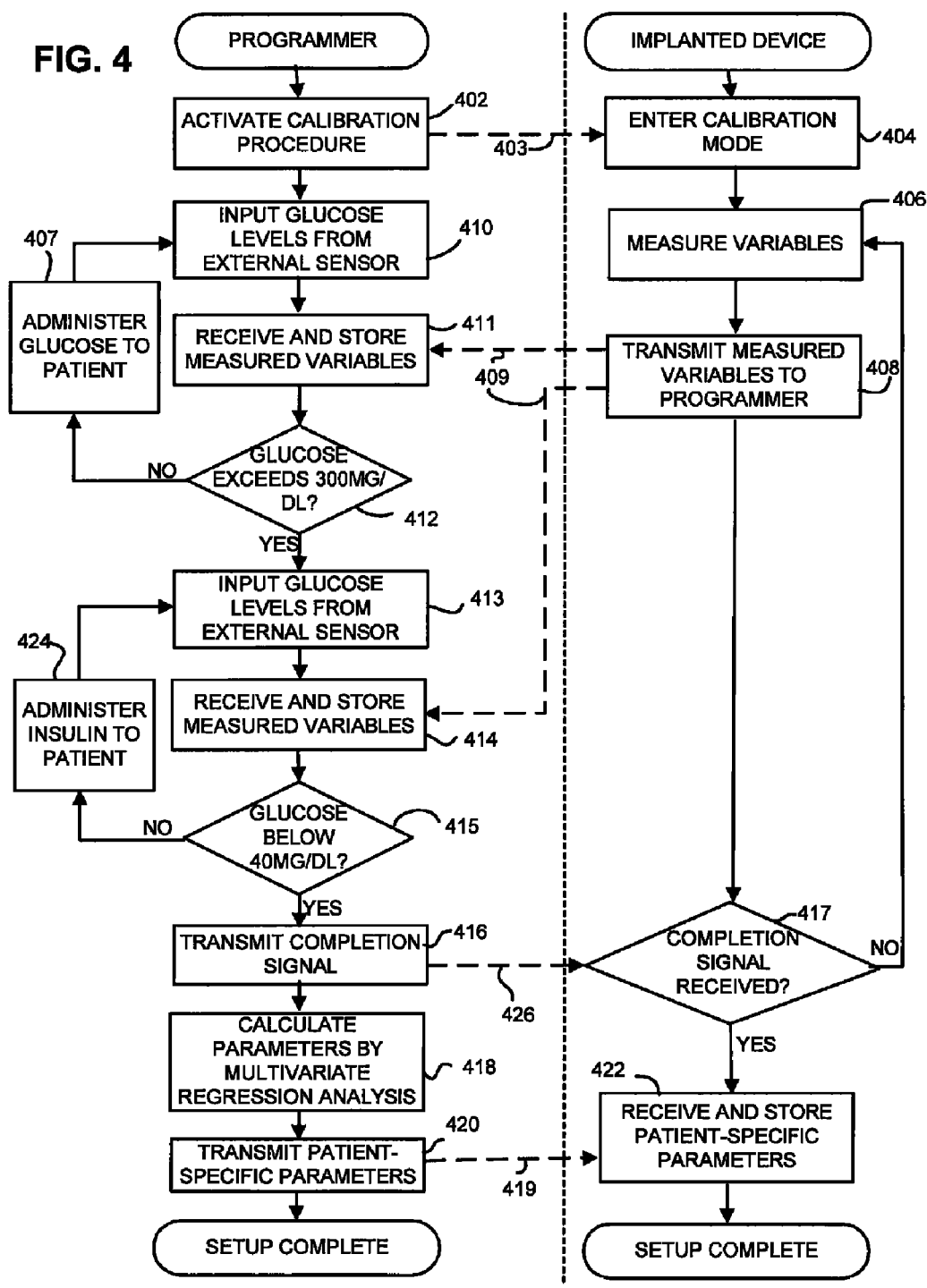
FIG. 4 is a flowchart illustrating a calibration technique performed by both the implantable stimulation device of FIG. 2 and the external programmer of FIG. 3 following implantation of the device for determining patient-specific parameters exploited by the technique of FIG. 5 in accordance with specific embodiments of the present invention.
Figure 5:
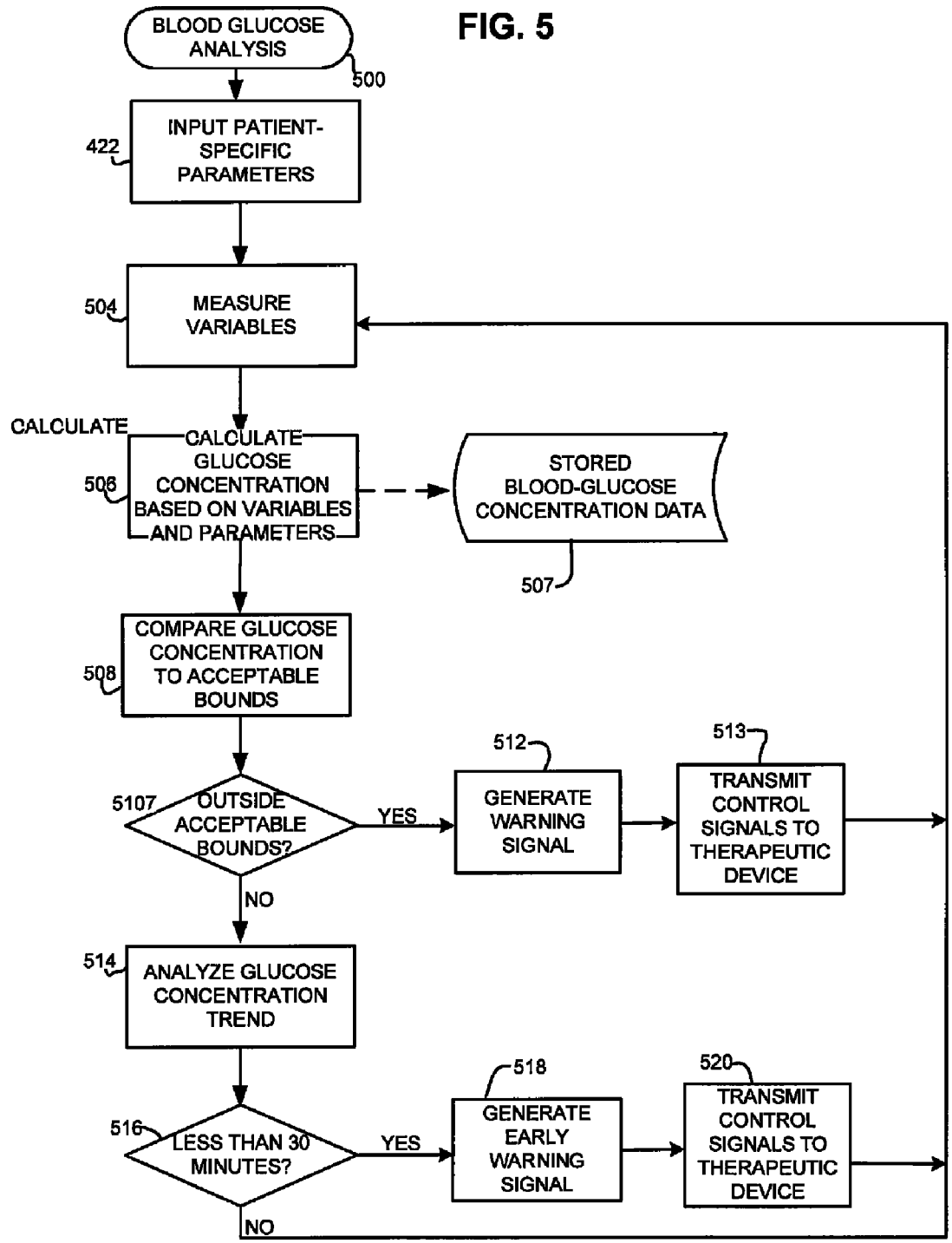
FIG. 5 is a flow diagram illustrating a method performed by the blood-glucose analysis unit of FIG. 2 to calculate blood-glucose concentration in accordance with specific embodiments of the present invention.

In FIGS. 4 and 5, flow charts are provided illustrating the operation and novel features of various exemplary embodiments of the invention. In the flow charts, various algorithmic steps are summarized in individual "blocks". Such blocks describe specific actions or decisions to be made or carried out as the algorithm proceeds. Where a microcontroller (or equivalent) is employed, the flow charts presented herein provide the basis for a "control program" that may be used by such a microcontroller (or equivalent) to effectuate the desired control of the device. Those skilled in the art may readily write such a control program based on the flow charts and other descriptions presented herein.

FIG. 4 is a flowchart illustrating one embodiment of a calibration technique for use in determining patient-specific parameters for subsequent use by the blood-glucose analysis unit 268 of FIG. 2 when performing the steps of FIG. 5. FIG. 4 illustrates steps performed by the programmer 202 of FIG. 3 and by the implantable stimulation device 110 of FIGS. 1 and 2 with steps performed by the programmer 202 shown on the left and steps performed by the implantable stimulation device 110 shown on the right. Initially, at step 402, upon input of appropriate activation commands by a physician or clinician operating the programmer 202, the blood-glucose calibration unit 350 initiates the calibration procedure and transmits a signal to the implantable stimulation device 110 for controlling the blood-glucose analysis unit 268 of the implantable stimulation device 110 to enter a calibration mode, at step 404. In the calibration mode, the blood-glucose analysis unit receives heart-rate, stroke volume, oximetry values, PPG values, temperature measurements and other physiological variables from sensors and electrocardiographic signals, at step 406, but does not calculate blood-glucose concentration. (Blood-glucose analysis unit 268 does not calculate blood-glucose concentration because it does not yet have the patient-specific parameters needed to calculate the blood-glucose concentration). Rather, at step 408, the implantable stimulation device simply transmits the measured variables 409 to programmer 202. Steps 406 and 408 are repeated in a loop until a completion signal is ultimately received.

Meanwhile, at step 410, blood-glucose concentration calibration unit 350 of the programmer 202 inputs blood-glucose concentrations derived from an external blood-glucose concentration monitor 329 while the physician delivers glucose to the patient either orally or intravenously for the purposes of raising the blood-glucose concentration at step 407. Alternatively, if the patient is an insulin-dependent diabetic, the physician merely withholds insulin that would otherwise be provided to thereby allow the blood-glucose concentration to rise. The blood-glucose concentration measured at step 410 may be received automatically from an external blood-glucose concentration monitor 329 that is directly coupled to programmer 202 or may be input manually by the physician based on information provided by the external blood-glucose concentration monitor. Any of a variety of commercially available external blood-glucose concentration monitors may be employed. Preferably, an external blood-glucose concentration monitor 329 is employed that is capable of substantially continuously monitoring and updating the blood-glucose concentration such that data can be input substantially continuously at step 410 to provide a precise record of blood-glucose concentration as a function of measured electrocardiographic data, oximetry values and other physiological values. Alternatively, the blood-glucose concentration may be calculated and input periodically, such as once every 10 to 15 minutes. In any case, the blood-glucose concentrations provided by the external blood-glucose concentration monitor 329 are recorded in the memory of programmer 202 for subsequent use. Electrocardiographic values, oximetry values and other physiological variables 409 from the implantable stimulation device 110 are received and stored at step 411. The blood-glucose concentration for the patient is allowed to rise until it exceeds 300 mg/dl. When the blood-glucose concentration exceeds 300 mg/dL at step 412, programmer 202 moves on to step 413.

Beginning at step 413, the physician delivers insulin to the patient at step 424 to cause the blood-glucose concentration to decrease while programmer 202 continues to receive and store the blood-glucose concentration for the patient derived from the external monitor and continues to receive and store, at step 414, cardiac output, oximetry values and other physiological variables 409 measured by the implantable stimulation device 110. The patient's blood-glucose concentration is allowed to decrease until it falls below 40 mg/dl at step 415. When the patient blood-glucose concentration is below 40 mg/dl the data collection process is complete and a completion signal 426 is transmitted to the implantable stimulation device 110 at step 416. Upon receipt of the completion signal 426 at step 417, the implantable stimulation device 110 may suspend detection of cardiac output, oximetry values and other physiological variables 409.

The patient-specific parameters 419 of the relationship function are then calculated by programmer 202 at step 418 using the metabolic oxygen conformation method. In accordance with one embodiment of the metabolic oxygen conformation method, programmer 202 records data that provides the cardiac output, oximetry values and other physiological variables 409, for each input blood-glucose concentration throughout the range of 40 to 300 mg/di during steps 410 to 416. At step 418, the blood-glucose concentration calibration unit 350 uses the metabolic oxygen conformation method to automatically determine a set of parameters that relate a selected group of the recorded oxymetric, electrocardiographic and physiological variables 409 to the actual recorded patient blood-glucose concentrations. In one embodiment of the invention, the parameters of the relationship function "F" are determined by using otherwise conventional regression analysis.

In another example, rather than fitting the data to a predetermined mathematical relationship, programmer 202 instead generates a lookup table relating cardiac output, oximetry values and other physiological variables 409 to patient blood-glucose concentration. The lookup table may be generated by interpolating, if needed, between individual data values recorded during steps 402-416. The lookup table is then transmitted to the implantable stimulation device 110 so the implantable stimulation device 110 can look up a value for the blood-glucose concentration for each combination of cardiac output and oximetry values. Although the use of a lookup table is certainly feasible, it requires more data to be stored within the implantable stimulation device 110. As can be appreciated a wide range of techniques may be employed for mathematically relating the cardiac output, oximetry values and other physiological variables 409 to the measured blood-glucose concentration and no attempt is made herein to describe all possible techniques.

After the patient specific parameters of the relationship function have been calculated at step 418, they are transmitted to implantable stimulation device 110 at step 418. Implantable stimulation device 110 receives and stores the patient-specific parameters at step 422. Thereafter, implantable stimulation device 110 begins monitoring blood-glucose concentration using the techniques described with respect to FIG. 5. Although not shown, the programmer 202 can also input control parameters provided by the physician for transmission to the implantable stimulation device 110, at step 416, for use in controlling the implantable stimulation device 110 or the implanted drug pump or other therapeutic device based on patient blood-glucose concentration. For example, the control parameters may specify an optimal blood-glucose concentration so that the implantable stimulation device 110 can then control the drug pump 207 to adjust the amount of insulin delivered to the patient to achieve the optimal blood-glucose concentration. The control parameters may also specify the specific upper and lower bounds used for generating warning signals.

Referring now to FIG. 5, the operation of blood-glucose analysis unit 268 of FIG. 2 will be described. Initially, at step 422, the blood-glucose analysis unit receives and stores a set of parameters relating patient measured physiological variables to blood-glucose concentration. The parameters are preferably generated in advance using the method of FIG. 4, and then transmitted to the implantable stimulation device 110 by programmer 202 for storage in memory 294. The parameters are derived in advance using the metabolic oxygen conformation method. Particular parameters are calibrated for a user or cluster of users using regression analysis comparing conventionally-measured blood-glucose concentration to internally-measured physiological variables. One method of calibrating the parameters in accordance with the metabolic oxygen conformation method is described with respect to FIG. 4. The parameters are saved in memory 294 of implantable stimulation device 110. The implantable stimulation device 110 can thereafter continuously monitor blood-glucose concentration based on the measured oxymetric, electrocardiographic and other measured physiological variables and the stored patient-specific parameters.

At step 504, the implantable stimulation device 110 measures the physiological variables used for blood-glucose concentration analysis. These may include, by way of example, stroke volume, heart-rate, hematocrit, peripheral temperature, core temperature, venous oxygen saturation, arterial oxygen saturation, temperature, blood flow and blood pressure. The measured variables may, if desired or necessary be stored in memory 294 of implantable stimulation device 110.

At step 506, blood-glucose analysis unit 268 of host controller 260 calculates the current blood-glucose concentration in the blood of the patient based on the physiological variables measured in step 504 and the patient-specific parameters stored in step 422. The calculated blood-glucose concentration is then stored at step 507, and compared at step 508 against both an upper threshold and a lower threshold to ensure that the blood-glucose concentration is within acceptable bounds. In one example, the upper threshold is 120 mg/dl and the lower threshold is 60 mg/dl. The upper and lower threshold values are preprogrammed within the implantable stimulation device 110 and may be specified, for example, by a physician using programmer 202. If the blood-glucose concentration is found to be outside the acceptable bounds at step 510, a warning signal is generated at step 512 to alert the patient. A drug pump 207 or other therapeutic device can also be adjusted at step 512, as described in more detail below. At step 514, the rate of change of blood-glucose concentration is calculated and a time by which blood-glucose concentration will be out of bounds is calculated based on the current blood-glucose concentration and the rate of change. If the blood-glucose concentration is predicted to be outside the acceptable bounds within 30 minutes at step 516, an early warning signal is generated at step 518.

Steps 504-518 can be repeated at intervals to update the blood-glucose concentration measurement. For example, the measurement may be repeated once every minute, once every 15 minutes, or once every hour. Preferably, the interval between calculations of blood-glucose concentration is selected so as to maintain adequate control of blood-glucose concentration and programmed in advance by a physician using programmer 202. The interval between blood-glucose concentration measurement updates may also vary depending upon the glucose concentration, the rate of change of glucose concentration, or the activity of the subject. For example, if the rate of change of glucose concentration is determined to be high at step 514, the interval until the next update may be reduced compared to the normal update interval. Conversely, if the rate of change of glucose concentration is determined to be low at step 514, the interval until the next update may be increased compared to the normal update interval. Likewise, if the blood-glucose concentration is found to be below a threshold, such as 70 mg/di or above a threshold such as 110 mg/dl the interval until the next update may be reduced compared to the normal update interval. The reduced interval between updates thus allows for more accurate analysis of the current blood-glucose level during high risk periods, i.e. when blood glucose is changing rapidly or the subject is close to hypoglycemia or hyperglycemia.

Preferably, a different warning signal is provided at step 512 when the blood-glucose concentration is too low than when it is too high. Additionally, the early warning signal of step 518 is preferably different than the warning signal of step 512. The early warning signal of step 518 is preferably initially of a lower intensity than the warning signal of step 512 and may be designed to increase in intensity as the predicted time within which blood-glucose concentration will be out of acceptable bounds reduces towards zero. Depending upon the configuration of the implantable stimulation device 110, the warning signal may be generated by causing the pacemaker to periodically vibrate inside the patient. Alternatively, the pacemaker may transmit a warning signal to an external warning device such as a bedside monitor or a portable device 204 carried with the patient, which displays the warning for the patient.

If a warning signal is transmitted to an external warning device, the exact blood-glucose concentration is preferably also transmitted such that it can be displayed to the patient. Additionally, if the portable device 204 is provided with a wireless modem 732, the warning signal may also be transmitted through communications server 709 and WAN 364, to other persons, such as the device manufacturer, a physician, clinician, nurse or caregiver as described with respect to FIG. 7. In the alternative, if an external warning device is provided, the current blood-glucose concentration may be transmitted periodically such that the patient is kept apprised of the current blood-glucose concentration. In other words, this information is not transmitted only when the blood-glucose concentration falls outside acceptable bounds but is transmitted periodically. In addition, since the blood-glucose concentration is recorded in memory at step 506, this information may be subsequently transmitted to the programmer 202 device for review by a physician during a subsequent office visit. Note that a wide range of other diagnostic information is routinely detected and recorded by the implantable stimulation device 110, such as heart-rate and the like. Accordingly, the blood-glucose concentration of the patient can be correlated with other diagnostic information to help the physician develop optimal therapies for the patient and to better tune the blood-glucose concentration determination and warning parameters.

At steps 513 and 520, if a drug pump or other therapeutic device to control blood-glucose concentration has been implanted in the patient, blood-glucose analysis unit 268 transmits appropriate control signals to the drug pump to adjust the amount of insulin provided to the patient or level of therapeutic intervention in response to the blood-glucose concentration and rate of change of blood-glucose concentration. For example, if the blood-glucose concentration has exceeded the upper bound, the drug pump is controlled to provide a greater amount of insulin to the patient. As with the generation of warning signals, control of the drug pump is not limited only to circumstances in which the blood-glucose concentration has exceeded the acceptable bounds. Rather, each newly calculated value for blood-glucose concentration may be used to control the drug pump 207 to maintain the blood-glucose concentration at a target concentration deemed by the physician to be optimal such as, for example, at 100 mg/dl.

In one example, drug pump 207 is additionally controlled to modulate the blood-glucose concentration based upon the current activity level of the patient, for example, to increase the blood-glucose concentration whenever the patient is more active and to decrease it otherwise. The activity level may be inferred for example, from the rate of oxygen consumption determined from the stroke volume, heart-rate and oxymetry data. In another example, drug pump 207 is additionally controlled to deliver insulin based on the blood-glucose concentration and the rate of change of blood-glucose concentration. Additionally, other programmable features of the implantable stimulation device 110 may be adjusted based upon blood-glucose concentration and/or rate of change of blood-glucose concentration. As one example, if blood-glucose concentration is found to be particularly low, a base pacing rate may be reduced until the blood-glucose concentration returns to acceptable concentrations. A wide variety of techniques may be employed for controlling a drug pump 207 or for controlling various functions of the implantable stimulation device 110 and no attempt is made herein to describe all possible techniques.

The blood-glucose concentration calculated by blood-glucose analysis unit 268 is stored at step 507. The stored blood-glucose concentration data is used in order to analyze the rate of change of blood-glucose concentration as part of the blood-glucose concentration trend analysis of step 514. The stored blood-glucose concentration data may also be used to generate average blood-glucose concentration figures as a measure of the quality of blood-glucose regulation over time. In one example, average blood-glucose concentration may be calculated as a running average of its value over a certain time period (e.g., can be as long as three months). The HbA1c blood test is a measure of average blood-glucose concentration during the previous two to three months. The average blood-glucose concentration calculated by implantable device 110 over a two month to three month period can be used as a synthetic proxy for the HbA1c test and may be readily correlated to standard HbA1c test results. The average blood-glucose concentration may be calculated by implantable stimulation device 110 or implantable stimulation device 110 may generate and store daily blood-glucose concentration averages which can then be downloaded and averaged by programmer 202 or reader 203, or portable device 204. In this way, the overall effectiveness of blood-glucose concentration regulation can be monitored without requiring HbA1c blood tests.

Oxymetry and PPG Sensors

Referring now to FIG. 6A, there is shown an exemplary oxymeter 124 suitable for use in an embodiment of the present invention. In accordance with the present invention, blood-glucose concentration is calculated in part by measuring a proxy for glucose metabolism. Glucose metabolism is the primary use of oxygen in the human body. Hence, in the metabolic oxygen conformation method, oxygen consumption is used as a proxy for glucose metabolism. Oxygen consumption can be measured using a combination of implantable sensors. One way to analyze oxygen consumption is to measure the difference in the concentration of oxygen in the arterial blood and the venous blood and multiply by the cardiac output. Oxymeter 124 of FIG. 6A may be utilized to measure the concentration of oxygen in the blood utilizing a two step process: first determining blood-oxygen saturation; and second determining hematocrit. Blood-oxygen concentration is proportional to blood-oxygen saturation multiplied by hematocrit.

Blood-oxygen saturation is the relative amount of oxygenated hemoglobin in all of the hemoglobin present in the blood stream. This hemoglobin is packaged in biconcave discs of approximately 10 micrometers diameter which commonly occur with a density of approximately five million red blood cells per cubic millimeter. When radiant energy (e.g., light) is incident upon red blood cells, the red blood cells both scatter and transmit the incident radiant energy. The differential absorption by oxygenated and non-oxygenated hemoglobin of the radiant energy of particular wavelengths reflected by and transmitted through the red blood cells furnishes the basis for the oxygen saturation measurements.

An oxymeter uses light sources of two or more different centered wavelengths to obtain measures of blood-oxygen saturation by measuring the absorption and/or scattering of those wavelengths by oxyhemoglobin and reduced hemoglobin in the blood. The absorption and/or scattering is measured using a light sensor. The measured absorption and/or scattering data allows for the calculation of the relative concentration of reduced hemoglobin and oxyhemoglobin, and therefore blood-oxygen saturation levels, since the absorption and/or scattering relationships are known.

In addition to using the above described light sources and light sensors to measure levels of blood-oxygen saturation, they can also be used to measure levels of hematocrit, which refers to the percentage of packed red blood cells in a volume of whole blood. Various techniques are known for determining hematocrit based on scattered light. For example, light of about 500 nm and light of about 800 nm can be directed at a blood sample, and an algorithm can be used to calculate hematocrit based on the relative intensities of scattered light detected by a light sensor. In another technique, a pair of spatially-separated light sensors can be used to detect reflected infra red (IR) light, e.g., of 805 nm. The intensity of the IR light detected by the photo sensor that is nearer to the IR light source is referred to as IRnear, and the intensity of the IR light detected by the light sensor farther from the IR light source is referred to as IRfar. As described in an article by Bornzin et al., entitled "Measuring Oxygen Saturation and Hematocrit Using a Fiberoptic Catheter", *IEEE/9th Annual Conf of the Eng. & Biol. Soc.* (1997), which is incorporated herein by reference, the ratio: R=IRnear/IRfar is directly related to the level of hematocrit, but independent of oxygen saturation because 805 nm is an isobestic wavelength (a wavelength that is scattered and/or absorbed equally by oxygenated and deoxygenated hemoglobin.

In accordance with a specific embodiment of the present invention, the implantable oxymeter 124 includes an implantable housing 604 including a window 606 through which light can pass to fall on red blood cells 600. The term window, as used herein, is intended to collectively encompass all portions of the housing through which light of interest can enter and exit the housing, even if such portions are separated from one another (e.g., by opaque portions). Included within the housing are three light sources 608, one far light source 610, a measurement light sensor 612 and a calibration light sensor 614. One of each of the light sources 608 transmits light at each of the wavelengths 670 nm, 705 nm, and 805 nm. Far light source 610 transmits light at the isobestic wavelength 805 nm. The intensity of the light transmitted by each light source is controlled by a corresponding drive signal 607, 609 that drive the light sources 608 and far light source 610. The drive signal may be different for each of the three wavelengths emitted by light sources 608. A portion of the light of each wavelength exits the housing through the window 606. The measurement light sensor 612 detects light of each wavelength scattered back into the housing through the window 606, and produces a measurement signal 614 that is indicative of the intensity of the light of each wavelength detected by the measurement light sensor. A portion of window 606 above calibration sensor 614 is provided with a reflective surface 620 to reflect some but not all of the light waves onto the calibration light sensor 614. The calibration light sensor detects a portion of the light of each wavelength that has not exited the housing and produces a calibration signal 616 that is indicative of the intensity of the light of the wavelength detected by the calibration light sensor 614, which is indicative of the intensity of the light transmitted by each light source.

In accordance with specific embodiments, a controller adjusts drive signals 607, 609 based on the calibration signal 616, to keep the intensity of the light transmitted by each light source substantially constant. In accordance with other embodiments of the present invention, a controller adjusts the measurement signal 614, based on the calibration signal, to compensate for changes in the intensity of the light transmitted by each light source 608, 610. In still other embodiments, rather than adjusting signals, the oxymetry processing unit 264 (that uses the measurement signal for a diagnostic and/or therapeutic purpose) detects changes in the intensity of the light transmitted by each light source based on the calibration signal 614, and takes into account the changes in intensity when using the measurement signal 614 for a diagnostic and/or therapeutic purpose. For example, the oxymetry processing unit 264 can take such changes in intensity into account by making appropriate adjustments to algorithms that are used to determine levels of blood-oxygen saturation and/or levels hematocrit based on the measurement signal.

ASIC 622 comprises a plurality of digital to analog converters and analog to digital converters for providing the drive signals 607, 609 to drive the light sources 608 and far light source 610 and receive the measurement signal 614 and calibration signal 616. ASIC 622 communicates a digital representation of the measurement signal 614 and calibration signal 616 for each of light sources 608 and far light source 610 to implantable stimulation device 110 via right atrial lead 120 and receives power from implantable stimulation device 110 via right atrial lead 120. Lead 120 comprises one or more conductive wires to connect ASIC 622 to implantable stimulation device 110.

More detailed descriptions of oxymeters suitable for use in the present invention may be found in copending patent application U.S. Ser. No. 11/282,198 filed Nov. 17, 2005 entitled "Implantable Self Calibrating Optical Sensors" and invented by John W. Poore, which is incorporated herein by reference. Moreover, oxymeter as used herein is not to be limited to the particular oxymeter disclosed herein. Blood-oxygen concentration may be measured by several technologies. As used herein "oxymeter" should be interpreted to encompass any device or technology that can be used to determine oxygen concentration in the blood.

Referring again to FIG. 6A, housing 604 of oxymeter 124 is also shown to enclose temperature sensor 624. Temperature sensor 624 may comprise any electronic device for measuring temperature. Suitable devices include, but are not limited to, thermopiles, thermistors, thermocouples. Thermopiles measure temperature by measuring IR radiation incident of the detector surface. Thus, if a thermopile is used as temperature sensor 624, a window transparent to IR (not shown) must be provided to allow heat/IR radiation from the blood to fall on the surface of the detector. Thermistors and thermocouples may measure temperature by conduction. Such temperature measuring devices should therefore be placed in good thermal contact with the blood. As shown in FIG. 6A, temperature sensor 624 may be place in contact with housing 604 of oxymeter 124. Housing 604 is preferably made of metal. As housing 604 is in good thermal contact with the blood and with temperature sensor 624, and because metal is a good conductor of heat, temperature sensor 624 can accurately measure the temperature of the blood. Although temperature sensor 624 is shown as part of oxymeter 124, a separate temperature sensor device may be used.

Referring again to FIG. 1, in one embodiment of the present invention, oxymeter 124 can be designed for implantation in the right atrium 102 of a heart 100. The right atrium of the heart receives deoxygenated blood from the body by way of the superior and inferior vena cava. The deoxygenated blood is pumped from the right atrium 102 to the right ventricle 104 and thence to lungs where it is re-oxygenated. Thus, measuring the concentration of oxygen in the blood in the right atrium 102 or right ventricle 104 reveals how much oxygen was used by the body since that blood was last pumped through the lungs. The right atrium is an ideal location for the oxymeter because in the right atrium all the venous blood from the entire body is mixed. However, oxymeter 124 could be located in the inferior or superior vena cava instead of the right atrium although the results may not be quite so complete. In order to minimize the number of implantable devices, oxymeter 124 (not shown) is preferably built into implantable right atrial lead 120 which is already to be implanted into the right atrium. If desired or necessary a second oxymeter may be provided to monitor the arterial oxygen concentration in blood returning from the lungs via the pulmonary veins to the left atrium. In such case, an oxymeter as described above may be included in left atrial sensor 152. An oxymeter, as described above, could also be mounted externally on the housing 112 of implantable stimulation device 110 to measure oxygen saturation of the blood perfusing the tissues surrounding the implantable stimulation device 110.

Referring now to FIGS. 6B-C which illustrate a photoplethysmography ("PPG") sensor built into the housing 112 of implantable stimulation device 110. FIG. 6B shows an embodiment of a PPG sensor 211 which can also be used to measure oxygen saturation. As shown in FIG. 6B, PPG sensor 211 comprises a light source 632, which preferably comprises parallel and oppositely oriented red and infrared LEDs positioned such that light is directed into the overlying tissue, and a light detector 634, preferably a photodiode, positioned such that it collects light reflected by the overlying tissue. The electronic circuitry associated with the light source and sensor is well known for external pulse oxymeters, and is described in, e.g., U.S. Pat. No. 4,869,254 entitled, "Method And Apparatus For Calculating Arterial Oxygen Saturation" to Stone et al., and U.S. Pat. No. 5,078,136, entitled, "Method And Apparatus For Calculating Arterial Oxygen Saturation Based Plethysmographs Including Transients" to Stone et al. which are incorporated herein by reference. Alternate embodiments of the PPG sensor for oxygen saturation analysis may use more than two wavelengths, for example, as described with respect to the oxymeter of FIG. 6A. Alternatively, a single wavelength driven at two different current levels might be used, such as in the technique described in U.S. Pat. No. 4,815,469 entitled "Implantable Blood Oxygen Sensor And Method Of Use" to Cohen et al. which is incorporated herein by reference.

Returning to the embodiment of the combined vascular plethysmography and $O_2$ saturation sensor shown in FIG. 6B, the source 632 and detector 634 are placed in a well 640 and that is created when the monitor housing 112 is machined, formed, or cast. In the preferred embodiment well 640 is formed using the minimum volume necessary to contain its feed through connector and optical device. A light barrier 636 is position between the source and detector to ensure that no light passes directly between them. The source and the detector are physically positioned such that the amount of light received at the detector is maximized. In particular, they are angled toward each other such that the direction of greatest optical power and sensitivity are aligned. Furthermore, in the preferred embodiment the optical devices have inherent directionality to avoid the need for lenses or other focusing elements, though these are used in alternate embodiments. The remaining space in the well is filled with epoxy such that the surface of the monitor 20 is smooth and flat, thereby minimizing the risk of tissue trauma and infection. The optical source 26 and detector 28 are connected via feed-through connections 642 and 644 to PPG Processing Circuit 265 thus ensuring hermeticity.

The light source 632 and the light detector 634 are preferably placed on the side of the implantable stimulation device 110 that, following implantation faces the chest wall, and are configured such that light cannot pass directly from the source to the detector. Thus, the reflection configuration is preferably used when the plethysmography device is implemented in an implantable device. The placement on the side of the device that faces the chest wall maximizes the signal to noise ratio by 1) directing the signal toward the highly vascularized musculature, and 2) shielding the source and detector from ambient light that enters the body through the skin. Alternatively, at the risk of increasing susceptibility to ambient light, the light source 632 and the light detector 634 can be placed on the face of the device that faces the skin of the patient.

The light source 632 can transmit light of more than one wavelength. For example, in an embodiment of the present invention the light source 632 transmits light having a first wavelength and light having a second wavelength. More specifically, in one embodiment light source 362 outputs visible red light e.g., 660 nm wavelength and outputs an infrared or near infrared light signal e.g., 940 nm wavelength. In this embodiment, the light output from light source 632 is serially pulsed to produce an interleaved light stream that is detected by light detector 634. The light stream consists of interleaved visible red light and infrared radiation. The interleaved signal stream is reflected from tissue of a patient and light is received by light detector 634. As the light is reflected from tissue, some of the energy is absorbed by arterial and venous blood, tissue and the variable pulsations of arterial blood. Analog signals representative of the reflected light of the two wavelengths are converted to digital signals and transmitted to PPG processing unit 265 of host controller 260. PPG processing unit 265 calculates blood oxygenation levels based on these signals. The blood oxygenation level in the tissues of the subclavian pocket adjacent the implantable stimulation device 110 may be used as a measure of arterial oxygen saturation. It is noted that the term "light" refers to both visible and non-visible light, with light being further defined, when necessary, by specific wavelengths (e.g., visible red or infrared). Additional details of implantable PPG devices suitable for use as a PPG sensor in embodiments of the present invention are disclosed in U.S. Pat. No. 6,491,639, entitled "Extravascular Hemodynamic Sensor" to Turcott, U.S. Pat. No. 6,731,967, entitled "Methods And Devices For Vascular Plethysmography Via Modulation Of Source Intensity" to Turcott, and U.S. Pat. No. 6,997,879, entitled "Methods And Devices For Reduction Of Motion-Induced Noise In Optical Vascular Plethysmography" to Turcott which are incorporated herein by reference.

Referring again to FIG. 6C a temperature sensor 210 is shown in contact with housing 112. Temperature sensor 210 may comprise any electronic device for measuring temperature. Suitable devices include, but are not limited to, thermopiles, thermistors, thermocouples. Thermopiles measure temperature by measuring IR radiation incident of the detector surface. Thus, if a thermopile is used as temperature sensor 210, a window transparent to IR (not shown) must be provided to allow heat/IR radiation from the blood to fall on the surface of the detector. Thermistors and thermocouples may measure temperature by conduction. Such temperature measuring devices should therefore be placed in good thermal contact with the blood. As shown in FIG. 6C, temperature sensor 210 may be place in contact with housing 112 of implantable stimulation device 110. Housing 112 is preferably made of metal. As housing 112 is in good thermal contact with the tissue of the subclavian pocket adjacent the implantable stimulation device 110 and with temperature sensor 210, and because metal is a good conductor of heat, temperature sensor 624 can accurately measure the temperature of the body in the subclavian pocket as a measure of peripheral temperature. Although temperature sensor 210 is shown as part of implantable stimulation device 110 a separate temperature sensor device may be used external to the housing and connected via a lead.

Data Entry and Network Communication

Figure 7:
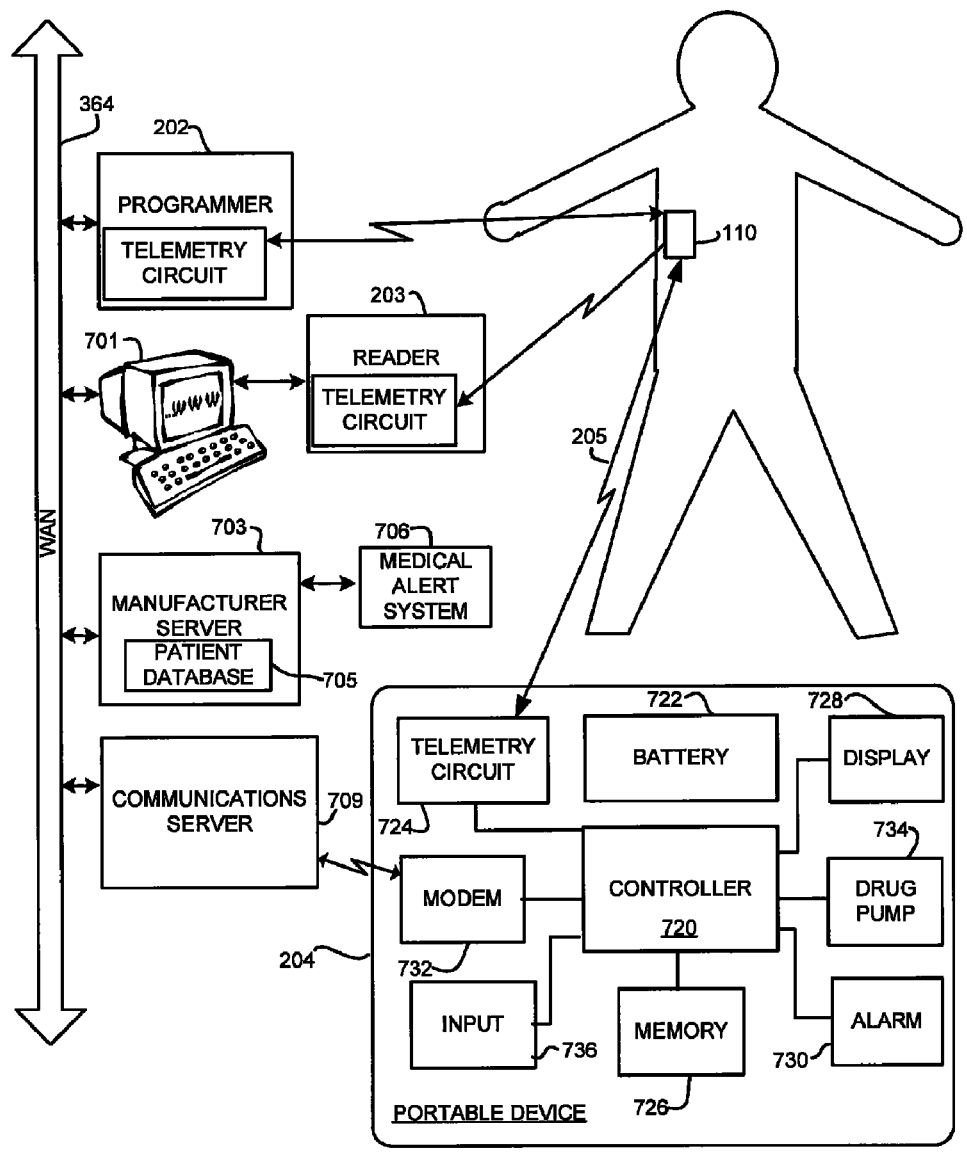
FIG. 7 shows a network communication system for use with the implantable stimulation device of FIGS. 1 and 2.

Referring now to FIG. 7, where a network system comprised of the implantable stimulation device 110 and a number of devices with which it may communicate are shown. As previously discussed, implantable stimulation device 110 may communicate via telemetry circuit 201 with programmer 202. In addition, the patient may be provided with a reader 203 which has its own telemetry circuit which may receive information from implantable stimulation device 110. Reader 203 may be, for example, a peripheral device connected to a patient's general purpose computer. Computer system 701 preferably comprises software for initiating transfer of data via reader 203 from implantable stimulation device 110. The software should also be able to accept data input by the patient using a standard computer keyboard. For example, the patient might be asked to keep a diary of foods consumed, exercise undertaken, subjective energy levels and qualitative feelings of healthfulness. This patient entered information may be correlated with the records of blood-glucose concentration and other physiological data downloaded from the implantable stimulation device 110. Based on correlations between the patient entered data and the physiological data and calculated blood-glucose concentrations, the computer system could provide advice to the patient as to how to better maintain blood-glucose concentration. In addition, computer system 701, if provided with a modem or NIC, can communicate the patient entered data and downloaded blood-glucose concentration onto a Wide Area network (WAN) 364. WAN 364 may communicate the data to the computer system of a physician, healthcare provider, or the manufacturer of the implantable stimulation device. One way to achieve this is for computer system 701 to communicate the data to manufacturer server 703. Manufacturer server 703 includes a patient database 704 which provides information regarding the patient and implantable stimulation device 110, including communication addresses for the physicians, healthcare providers and caregivers of the patient. Manufacturer server 703 can then forward the data to the individuals identified in the patient database via the WAN 364. For example, the data may be forwarded to programmer 202 under the control of a physician where the data can be used to readjust the programmed parameters of implantable stimulation device 110 upon the patient's next visit to the physician. In addition, should the data indicate a serious and immediate problem, the manufacturer server 703, may instead communicate the data and patient data to Medical Alert System 706 which may act by multiple communication channels, such as paging, telephone etc to contact the physician, clinician, nurse, or caregiver of the patient to alert them of said serious an immediate problem or contact emergency services.

Alternatively or additionally, the patient may carry portable device 204. Portable device 204 may have the same general components as a wireless PDA with the addition of a telemetry circuit 724 for receiving information from implantable stimulation device 110. As shown in FIG. 7, portable device 204 comprises a controller 720, battery 722, telemetry circuit 724, memory 726, display 728, alarm 730, and wireless modem 732. Portable device 204 may also include an external drug pump 734 for supplying e.g. insulin to the patient if the patient does not have an implantable drug pump 207. In operation, Portable device 204 is carried by the patient close to implantable stimulation device 110 to allow for reliable communication with implantable stimulation device 110 via telemetry circuit 724. The communication may be initiated by the portable device—with or without user intervention or by implantable stimulation device 110. Blood-glucose concentration information and other physiological data may be downloaded from implantable stimulation device 111 to portable device 204. In addition, portable device 204 preferably comprises data entry means by which the patient may enter subjective health data. The downloaded and entered information may then by transmitted via the wireless modem to a communication server and thence via WAN 364 to the manufacturer server 705. This data may be forwarded by manufacturer server 703 in the same way as previously discussed. In addition, in certain circumstances, it may be desirable to upload external data from the portable device 204 to the implantable stimulation device 111 over a communication link 205. Such external data may include, for example, data entered by the subject, caregiver or physician indicating well-being, activity level, consumption of food or administration of insulin. Such external data could also include for example, data from sensors included in or connected to the portable device, such as temperature sensors, pulse sensors, light sensors and the like. Implantable stimulation device 111 may use such external data as input into the calculation of glucose concentration or to modify the parameters or to adjust the thresholds for alerts.

Additionally, portable device 204 may display blood-glucose concentration to the patient and thus advise the patient for example, whether a hypoglycemic event is imminent and thus to consume something to raise the blood-glucose concentration. Portable device 204 is preferably provided with an alarm 730 which is a device such as a vibrator, beeper or flashing light to draw attention of the patient to the portable device in order to provide information. Where blood-glucose concentrations are provided on a regular basis to portable device 204, steps 508-514 of FIG. 5 may be performed by the portable device including providing the warnings of steps 512 and 518.

The previous description of the preferred embodiments is provided to enable any person skilled in the art to make or use the embodiments of the present invention. While the previous description has described an embodiment of the present invention which includes cardiac stimulation abilities as well as blood-glucose concentration measurement, it is to be understood that a stand alone blood-glucose concentration measurement device may be made without departing from the spirit and scope of the invention. While the invention has been particularly shown and described with reference to preferred embodiments thereof, it will be understood by those skilled in the art that various changes in form and details may be made therein without departing from the spirit and scope of the invention.

What is claimed is:

1. A method comprising:
monitoring blood-glucose concentration in blood of a subject using a system implanted in a subject wherein the system has stored relationships therein between blood-glucose concentration and at least a first physiological metric, and wherein the system implanted in the subject performs the steps of (a) obtaining a measure of the first physiological metric using one or more sensors of the system implanted in the subject; and
(b) calculating the blood-glucose concentration using the stored relationships and the measure of the first physiological metric without using a measure obtained from an enzymatic sensor;
wherein the first physiological metric is a blood oxygen metric.

2. The method of claim 1, wherein:
the implanted system has stored relationships therein between blood-glucose concentration, the first physiological metric, and a second physiological metric,
step (a) comprises obtaining a measure of the first physiological metric and also a measure of the second physiological metric using one or more sensors and/or electrodes of the system implanted in the subject;
step (b) comprises calculating the blood-glucose concentration using the stored relationships, the measure of the first physiological metric, and also the measure of the second physiological metric without using a measure obtained from an enzymatic sensor; and
the second physiological metric is a metric, other than the first physiological metric, selected from the group consisting of a metric of venous oxygen saturation, a metric of arterial oxygen saturation, a metric of hematocrit, a metric of core temperature, a metric of peripheral temperature, a metric of blood pressure, a metric of blood flow, and a metric of heart rate.

3. The method of claim 2, wherein:
the system has stored relationships therein between blood-glucose concentration, the first physiological metric, the second physiological metric, and a third physiological metric,
step (a) comprises obtaining a measure of the first physiological metric, a measure of the second physiological metric and also a measure of the third physiological metric using one or more sensors and/or electrodes of the system implanted in the subject;
step (b) comprises calculating the blood-glucose concentration using the stored relationships, the measure of the first physiological metric, the measure of the second physiological metric and also the measure of the third physiological metric without using a measure obtained from an enzymatic sensor; and
the third physiological metric is a metric, other than the first and second physiological metrics, selected from the group consisting of a metric of venous oxygen saturation, a metric of arterial oxygen saturation, a metric of hematocrit, a metric of core temperature, a metric of peripheral temperature, a metric of blood pressure, a metric of blood flow, and a metric of heart rate.

4. The method of claim 1, wherein the first physiological metric is a metric of venous oxygen saturation, and the measure of the first physiological metric is obtained using an oxymeter implanted in the subject.

5. The method of claim 2, wherein the first physiological metric is a metric of venous oxygen saturation, and the measure of the first physiological metric is obtained using an oxymeter implanted in the subject.

6. The method of claim 5, wherein the second physiological metric is one of a metric of core temperature and a metric of peripheral temperature, and the measure of the second physiological metric is obtained using a temperature sensor implanted in the subject.

7. The method of claim 5, wherein the second physiological metric is a metric of blood pressure, and the measure of the second physiological metric is obtained using a blood pressure sensor implanted in the subject.

8. The method of claim 3, wherein:
the first physiological metric is a metric of venous oxygen saturation, and the measure of the first physiological metric is obtained using an oxymeter implanted in the subject, and
the second physiological metric is a metric of one of core temperature and peripheral temperature, and the measure of the second physiological metric is obtained using a temperature sensor implanted in the subject.

9. The method of claim 2, wherein the first physiological metric is a metric of hematocrit, and the measure of the first physiological metric is obtained using an oxymeter implanted in the subject.

10. The method of claim 3, wherein:
the second physiological metric is a metric of blood pressure, and the measure of the second physiological metric is obtained using a blood pressure sensor implanted in the subject, and
the third physiological metric is a metric of heart rate, and the measure of the third physiological metric is obtained using one or more electrodes implanted in the subject.

11. The method of claim 1, wherein:
step (a) comprises obtaining a measure of the first physiological metric using one or more sensors of the system implanted in the subject and also receiving external data from an external device; and
step (b) comprises using the stored relationships, the measure of the first physiological metric and also the external data to calculate the blood-glucose concentration without using a measure obtained from an enzymatic sensor.

12. The method of claim 1, further comprising transmitting the blood-glucose concentration from the implanted system to an external system wherein the external system communicates the blood-glucose concentration to at least one member of the group consisting of: the subject, a physician, a clinician, a nurse, a caregiver and a manufacturer.

13. The method of claim 1, further comprising:
causing a warning which can be sensed by the subject if the blood-glucose concentration reaches a threshold.

14. The method of claim 1, further comprising:
determining the rate of change of blood-glucose concentration by determining the blood-glucose concentration at a plurality of times during a period; and
causing an alert which can be sensed by the subject in response to the rate of change of glucose concentration.

15. The method of claim 1, further comprising:
determining a metric indicative of average blood-glucose concentration during a period of time by determining the blood-glucose concentration at a plurality of times during the period of time.

16. The method of claim 1, wherein the implantable system provides electrical stimulation to an organ of the subject and wherein the method further comprises modifying the electrical stimulation in response to the blood-glucose concentration.

17. An implantable system for monitoring blood-glucose concentration in a subject wherein the system comprises:
a memory which has stored therein relationships between blood-glucose concentration and at least a first physiological metric;
a first sensor which obtains a measure of the first physiological metric; and
a controller which calculates the blood-glucose concentration using the stored relationships and the measure of the first physiological metric;
wherein the system is adapted to be implanted in a subject, the first sensor is an implantable oxymeter, and the first physiological metric is a blood oxygen metric; and
wherein the system does not include an enzymatic sensor.

18. The system of claim 17, wherein the first sensor is an oxymeter adapted to be implanted in the subject and which obtains a measure of one of venous oxygen saturation, hematocrit, and arterial oxygen saturation.

19. The system of claim 18, further comprising:
a second sensor which obtains a measure of a second physiological metric;
wherein the memory has stored therein relationships between blood-glucose concentration, the first physiological metric, and the second physiological metric;
wherein the second sensor which obtains the measure of the second physiological metric is a sensor, other than the first sensor, selected from a group consisting of an oxymeter adapted to be implanted in the subject which obtains a measure of venous oxygen saturation, an oxymeter adapted to be implanted in the subject which obtains a measure of hematocrit, an oxymeter adapted to be implanted in the subject which obtains a measure of arterial oxygen saturation, a temperature sensor adapted to be implanted in the subject which obtains a measure of peripheral temperature, a temperature sensor adapted to be implanted in the subject which obtains a measure of core temperature, a blood pressure sensor adapted to be implanted in the subject which obtains a measure of blood pressure, a blood flow sensor adapted to be implanted in the subject which obtains a measure of blood flow, and an electrode adapted to be implanted in the subject which obtains a measure of heart-rate; and
wherein the controller calculates the blood-glucose concentration using the stored relationships, the measure of the first physiological metric and also the measure of the second physiological metric.

20. The system of claim 19, further comprising:
a third sensor which obtains a measure of a third physiological metric;
wherein the memory has stored therein relationships between blood-glucose concentration, the first physiological metric, the second physiological metric, and the third physiological metric;
wherein the third sensor which obtains the measure of the third physiological metric is a sensor, other than the first and second sensors, selected from the group consisting of an oxymeter adapted to be implanted in the subject which obtains a measure of venous oxygen saturation, an oxymeter adapted to be implanted in the subject which obtains a measure of hematocrit, an oxymeter adapted to be implanted in the subject which obtains a measure of arterial oxygen saturation, a temperature sensor adapted to be implanted in the subject which obtains a measure of peripheral temperature, a temperature sensor adapted to be implanted in the subject which obtains a measure of core temperature, a blood pressure sensor adapted to be implanted in the subject which obtains a measure of blood pressure, a blood flow sensor adapted to be implanted in the subject which obtains a measure of blood flow, and an electrode adapted to be implanted in the subject which obtains a measure of heart-rate; and
wherein the controller uses the stored relationships, the measure of the first physiological metric, the measure of the second physiological metric, and also the measure of the third physiological metric to calculate the blood-glucose concentration.

21. The system of claim 18, wherein the second sensor is a temperature sensor adapted to be implanted in the subject and which obtains a measure of one of core body temperature and peripheral body temperature.

22. A method performed by an external device in conjunction with an implantable medical device implanted within a subject, the method comprising:
obtaining, using the external device, a blood-glucose concentration of the subject at each of a plurality of times, to thereby obtain a plurality of different blood-glucose concentrations;
obtaining, using the implantable medical device, measures of one or more physiological metrics at each of the plurality of times;
transmitting, from the implantable medical device to the external device, data indicative of the measures of said one or more physiological metrics obtained at the plurality of times;
determining, using the external device, from the data indicative of the measures of said one or more physiological metrics at the plurality of times, parameters which enable the implantable medical device to derive blood-glucose concentrations for the subject from subsequently-obtained measures of said one or more physiological metrics;
transmitting the parameters to the implanted device; and
determining, using the implantable medical device implanted within a subject, the blood-glucose concentration of the subject, using the parameters and the subsequently-obtained measures of said one or more physiological metrics;
wherein said one or more physiological metrics include at least one blood oxygen metric.

23. The method of claim 22, wherein said one or more physiological metrics include at least two physiological metrics selected from the group consisting of a metric of venous oxygen saturation, a metric of arterial oxygen saturation, a metric of hematocrit, a metric of core temperature, a metric of peripheral temperature, a metric of blood pressure, a metric of blood flow, and a metric of heart rate.

24. The method of claim 22, wherein said one or more physiological metrics include at least three physiological metrics selected from the group consisting of a metric of venous oxygen saturation, a metric of arterial oxygen saturation, a metric of hematocrit, a metric of core temperature, a metric of peripheral temperature, a metric of blood pressure, a metric of blood flow, and a metric of heart rate.

25. The method of claim 22, wherein said one or more physiological metrics include at least a metric of venous oxygen saturation.

26. The method of claim 22, wherein the method further comprises:
administering glucose to the subject, during the obtaining with the implantable device of the measures of said one or more physiological metrics at the plurality of times, in order to increase the blood-glucose concentration of the subject between one of said plurality of times and another of said plurality of times.

27. The method of claim 22, wherein the method further comprises:
administering insulin to the subject, during the obtaining with the implantable device of the measures of said one or more physiological metrics at the plurality of times, in order to decrease the blood-glucose concentration of the subject between one of said plurality of times and another of said plurality of times.

28. A method comprising:
monitoring blood-glucose concentration in blood of a subject using a system implanted in the subject, wherein the system has stored relationships therein between blood-glucose concentration and a first physiological metric, a second physiological metric, and a third physiological metric, and wherein the system implanted in the subject performs the steps of:
(a) obtaining, using one or more sensors and/or electrodes of the system implanted within the subject,
a measure of the first physiological metric which is a physiological metric selected from the group consisting of a metric of venous oxygen saturation and a metric of hematocrit,
a measure of the second physiological metric which is a physiological metric, other than the first physiological metric, selected from the group consisting of a metric of hematocrit, a metric of core temperature, a metric of peripheral temperature, a metric of blood pressure, a metric of blood flow, and a metric of heart rate, and
a measure of the third physiological metric which is a metric, other than the first and second physiological metrics, selected from the group consisting of a metric of hematocrit, a metric of blood pressure, a metric of blood flow, and a metric of heart rate; and
(b) calculating the blood-glucose concentration using the stored relationships, the first physiological metric, the second physiological metric, and the third physiological metric.

29. The method of claim 28, wherein the first physiological metric is a metric of venous oxygen saturation, and the measure of the first physiological metric is obtained using an oxymeter implanted in the subject.

30. The method of claim 28, wherein:
the first physiological metric is a metric of venous oxygen saturation, and the measure of the first physiological metric is obtained using an oxymeter implanted in the subject; and
the second physiological metric is a metric of blood pressure, and the measure of the second physiological metric is obtained using a blood pressure sensor implanted in the subject.

31. The method of claim 28, wherein:
the first physiological metric is a metric of venous oxygen saturation, and the measure of the first physiological metric is obtained using an oxymeter implanted in the subject; and
the second physiological metric is one of a metric of core temperature and peripheral temperature, and the second physiological metric is obtained using a temperature sensor implanted in the subject.

32. The method of claim 28, wherein the first physiological metric is a metric of hematocrit, and the measure of the first physiological metric is obtained using an oxymeter implanted in the subject.

33. The method of claim 28, wherein:
the second physiological metric is a metric of blood pressure, and the measure of the second physiological metric is obtained using a sensor implanted in the subject; and
the third physiological metric is a metric of heart rate, and the measure of the third physiological metric is obtained using one or more electrodes implanted in the subject.

34. The method of claim 28, wherein step (b) comprises calculating the blood-glucose concentration using the stored relationships, the measure of the first physiological metric, the measure of the second physiological metric, and the measure of the third physiological metric, without using a measure obtained from an enzymatic sensor.

35. An implantable system for monitoring blood-glucose concentration in a subject wherein the implantable system comprises:
   a memory which has stored therein relationships between blood-glucose concentration and a first physiological metric, a second physiological metric, and a third physiological metric;
   one or more implantable sensors and/or electrodes which obtain,
      a measure of the first physiological metric, wherein the first physiological metric is a blood oxygen metric,
      a measure of the second physiological metric, wherein the second physiological metric is a metric, other than the first physiological metric, selected from the group consisting of a metric of venous oxygen saturation, a metric of hematocrit, a metric of arterial oxygen saturation, a metric of peripheral temperature, a metric of core temperature, a metric of blood pressure, a metric of blood flow, and a metric of heart-rate, and
      a measure of the third physiological metric, wherein the third physiological metric is a metric, other than the first and second physiological metrics, selected from the group consisting of a metric of venous oxygen saturation, a metric of hematocrit, a metric of arterial oxygen saturation, a metric of peripheral temperature, a metric of core temperature, a metric of blood pressure, a metric of blood flow, and a metric of heart-rate; and
   a controller which calculates the blood-glucose concentration using the stored relationships, the measure of the first physiological metric, the measure of the second physiological metric, and the measure of the third physiological metric.

36. The implantable system of claim 35, wherein the measure of the first physiological metric is obtained using an implantable oxymeter, and wherein the first physiological metric is selected from the group consisting of a metric of venous oxygen saturation, a metric of hematocrit, and a metric of arterial oxygen saturation.

37. The implantable system of claim 36, wherein the controller calculates the blood-glucose concentration using the stored relationships, the measure of the first physiological metric, the measure of the second physiological metric, and the measure of the third physiological metric, without using a measure obtained from an enzymatic sensor.

* * * * *